United States Patent
Burrows et al.

(10) Patent No.: US 10,251,982 B2
(45) Date of Patent: *Apr. 9, 2019

(54) BIOCOMPATIBLE, BIOMIMETIC AMPHOLYTE MATERIALS

(71) Applicant: BioInteractions Ltd., Reading (GB)

(72) Inventors: Fanny Burrows, Reading (GB); John E. Mckendrick, Reading (GB); Alan Rhodes, Reading (GB); Simon J. Onis, Reading (GB); Shivpal S. Sandhu, Farnham Common (GB)

(73) Assignee: BioInteractions Ltd., Reading (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/429,835

(22) Filed: Feb. 10, 2017

(65) Prior Publication Data

US 2017/0151375 A1    Jun. 1, 2017

Related U.S. Application Data

(63) Continuation of application No. 13/529,708, filed on Jun. 21, 2012, now Pat. No. 9,567,357.

(51) Int. Cl.

| | |
|---|---|
| *C08F 18/22* | (2006.01) |
| *A61L 33/00* | (2006.01) |
| *C08F 222/02* | (2006.01) |
| *A61L 27/34* | (2006.01) |
| *A61L 31/10* | (2006.01) |
| *C07F 9/10* | (2006.01) |
| *C07F 9/6574* | (2006.01) |
| *A61L 29/08* | (2006.01) |
| *A61L 29/14* | (2006.01) |
| *A61L 29/16* | (2006.01) |
| *A61L 31/14* | (2006.01) |
| *A61L 31/16* | (2006.01) |
| *A61L 33/06* | (2006.01) |
| *C08F 230/02* | (2006.01) |
| *C07F 9/09* | (2006.01) |
| *C08F 220/18* | (2006.01) |
| *C08F 220/28* | (2006.01) |
| *C09D 133/14* | (2006.01) |
| *G02B 1/04* | (2006.01) |
| *C07F 9/40* | (2006.01) |
| *C07F 9/06* | (2006.01) |
| *C07F 9/08* | (2006.01) |
| *C07F 9/32* | (2006.01) |
| *C07F 9/36* | (2006.01) |
| *C08F 130/02* | (2006.01) |

(Continued)

(52) U.S. Cl.
CPC ............ *A61L 33/0023* (2013.01); *A61L 27/34* (2013.01); *A61L 29/085* (2013.01); *A61L 29/14* (2013.01); *A61L 29/16* (2013.01); *A61L 31/10* (2013.01); *A61L 31/14* (2013.01); *A61L 31/16* (2013.01); *A61L 33/064* (2013.01); *C07F 9/091* (2013.01); *C07F 9/106* (2013.01); *C07F 9/6574* (2013.01); *C08F 220/18* (2013.01); *C08F 220/28* (2013.01); *C08F 222/02* (2013.01); *C08F 230/02* (2013.01); *C09D 133/14* (2013.01); *G02B 1/043* (2013.01); *C07B 2200/11* (2013.01); *C07F 9/062* (2013.01); *C07F 9/08* (2013.01); *C07F 9/32* (2013.01); *C07F 9/3205* (2013.01); *C07F 9/36* (2013.01); *C07F 9/40* (2013.01); *C07F 9/4078* (2013.01); *C08F 8/30* (2013.01); *C08F 8/40* (2013.01); *C08F 16/14* (2013.01); *C08F 18/22* (2013.01); *C08F 30/02* (2013.01); *C08F 116/14* (2013.01); *C08F 122/02* (2013.01); *C08F 130/02* (2013.01); *C08F 216/14* (2013.01); *C08F 2220/1825* (2013.01); *C08F 2220/281* (2013.01); *C08F 2220/285* (2013.01)

(58) Field of Classification Search
CPC ........ C08F 18/22; C08F 30/02; C08F 130/02; C08F 230/02; C08F 116/14; C08F 216/14; C08F 8/40; C08F 8/30
See application file for complete search history.

(56) References Cited

U.S. PATENT DOCUMENTS

| | | |
|---|---|---|
| 4,082,727 A | 4/1978 | Nagata et al. |
| 4,239,664 A | 12/1980 | Teng et al. |

(Continued)

FOREIGN PATENT DOCUMENTS

| | | |
|---|---|---|
| EP | 0032622 | 7/1981 |
| EP | 0036155 | 9/1981 |

(Continued)

OTHER PUBLICATIONS

Drescher et al., "Amino-Functionalized Single-Chain Bolalipids: Synthesis and Aggregation Behavior of New Basic Building Blocks", Biophysical Chemistry, vol. 150, pp. 136-143 (2010).

(Continued)

*Primary Examiner* — Ling Siu Choi
*Assistant Examiner* — David L Miller
(74) *Attorney, Agent, or Firm* — Christensen, Fonder, Dardi & Herbert PLLC; Curtis Herbert

(57) ABSTRACT

New ampholyte biomaterial compounds containing ampholyte moieties are synthesized and integrated into polymeric assemblies to provide hydrophilic polymers exhibiting improved biocompatibility, haemocompatibility, hydrophilicity non-thrombogenicity, anti-bacterial ability, and mechanical strength, as well as suitability as a drug delivery platform.

13 Claims, No Drawings

Related U.S. Application Data

(60) Provisional application No. 61/500,921, filed on Jun. 24, 2011.

(51) Int. Cl.

| | | |
|---|---|---|
| C08F 122/02 | (2006.01) |
| C08F 30/02 | (2006.01) |
| C08F 8/40 | (2006.01) |
| C08F 8/30 | (2006.01) |
| C08F 16/14 | (2006.01) |
| C08F 216/14 | (2006.01) |
| C08F 116/14 | (2006.01) |

(56) References Cited

U.S. PATENT DOCUMENTS

| | | |
|---|---|---|
| 4,331,697 A | 5/1982 | Kudo et al. |
| 4,367,155 A | 1/1983 | Birkelo |
| 4,987,181 A | 1/1991 | Bichon et al. |
| 5,183,872 A | 2/1993 | Heidel et al. |
| 5,344,455 A | 9/1994 | Keogh et al. |
| 5,462,976 A | 10/1995 | Matsuda et al. |
| 5,512,329 A | 4/1996 | Guire et al. |
| 5,583,213 A | 12/1996 | Yakuso et al. |
| 5,728,751 A | 3/1998 | Patnaik |
| 5,741,551 A | 4/1998 | Guire et al. |
| 5,741,881 A | 4/1998 | Patnaik |
| 5,763,504 A | 5/1998 | Matsuda et al. |
| 5,776,184 A | 7/1998 | Tuch |
| 5,783,570 A | 7/1998 | Yokota et al. |
| 5,837,747 A | 11/1998 | Soon-Shiong et al. |
| 5,846,530 A | 12/1998 | Soon-Shiong et al. |
| 5,855,618 A | 1/1999 | Patnaik et al. |
| 5,877,263 A | 3/1999 | Patnaik et al. |
| 5,945,457 A | 8/1999 | Plate et al. |
| 5,993,890 A | 11/1999 | Marchant et al. |
| 6,060,582 A | 5/2000 | Hubbell et al. |
| 6,096,798 A | 8/2000 | Luthra et al. |
| 6,121,027 A | 9/2000 | Clapper et al. |
| 6,127,348 A | 10/2000 | Roufa et al. |
| 6,344,576 B1 | 2/2002 | Eibl |
| 6,590,054 B2 | 7/2003 | Tanaka et al. |
| 2003/0021762 A1 | 1/2003 | Luthra et al. |

FOREIGN PATENT DOCUMENTS

| | | |
|---|---|---|
| EP | 0049828 A1 | 10/1981 |
| EP | 0049828 B1 | 10/1981 |
| EP | 0157469 | 10/1985 |
| JP | 58154591 | 9/1983 |
| JP | 59164331 | 9/1984 |
| JP | 59199696 | 11/1984 |
| JP | 62270591 | 11/1987 |
| JP | 2238007 | 9/1990 |
| JP | 63086704 | 4/1998 |
| JP | 63222183 | 6/1998 |
| JP | 63222185 | 9/1998 |
| JP | 2000128950 A | * 5/2000 |
| JP | 2003238647 A | * 8/2003 |
| WO | 9741164 | 11/1997 |

OTHER PUBLICATIONS

Drescher et al.,"General Synthesis and Aggregation Behaviour of New Single-Chain Bolaphospholipids: Variations in Chain and Headgroup Structures", Chemistry—A European Journal, vol. 14, pp. 6796-6804 (2008).
Furukawa et al.,"Note Polymeric Phospholipid Analogs. XXIV. Polymeric Phospholipid Analogs with Uridine Units", Journal of Macromolecular Science, vol. A25(3), pp. 337-343 (1988).
Hirota et al.,"Coating of a Surface with 2-Methacryloyloxyethyl Phosphorylcholine (MPG) Co-Polymer Significantly seduces Retention of Human Pathogenic Microorganisms", FEMS Microbiology Letters, vol. 248, pp. 37-45 (2005).
Hukins et al.,"Biomaterials: Defining the Mechanical Properties of Natural Tissues and Selection of Replacement Materials", Journal of Materials Chemistry, vol. 9, pp. 629-636 (1999).
Iwasaki et al.,"Phosphorylcholine-Containing Polymers for Biomedical Applications", Analytical and Bioanalytical Chemistry, vol. 381, pp. 534-546 (2005).
Kertscher et al., "Synthesis and Platelet-Aggregating Action of Some Structural Analogs of the Platelet-Activating Factor Having a Modified Head Group", Pharmazie, vol. 43 (1988).
Kiritoshi et al.,"Synthesis of Hydrophilic Cross-Linker Having Phosphorylcholine-Like Linkage for Improvement of Hydrogel Propreties", Polymer, vol. 45, pp. 7499-7504 (2004).
Kusumi et al.,"Dynamic and Structural Properties of Polymerized Phosphatidylcholine Vesicle Membranes", Journal of the American Chemical Society, vol. 105, pp. 2975-2980 (1983).
Nakaya et al.,"Phospholipid Polymers", Progress in Polymer Science, vol. 24, pp. 143-181 (1999).
Nakaya et al.,"Poly(phosphatidylcholine) Analogues", Macromolecules, vol. 22, pp. 3180-3181 (1989).
Nakaya et al.,"Synthesis and Polymerization of 2-{(2-Methacryloyloxy)-Ethyldimethyl-Ammonio}Ethyl p-Substituted Phenyl Phosphates", The British Liberary, pp. 207-215 (1994).
Tsubone et al.,"Syntheses of 2-(N-alkyl-N,N-dimethylammonio)ethyl Hydrogen Phosphates and Their Physicochemical Properties", Journal of the American Oil Chemists' Society, vol. 67(3) pp. 149-153 (1990).
Williams, "On the Nature of Biomaterials", Biomaterials, vol. 30, pp. 5897-5909 (2009).
Yamada et al.,"Synthesis and Polymerizatican of 2-{2-(Methacryloyloxy)Ethyl-Dimethlammonium}Ethyl n-Alkyl Phosphates", Chemistry Express, vol. 7(11), pp. 861-864 (1992).
Yasuzawa et al.,"Synthesis and Properties of Vinyl Polymers Containing Cholesterol and Phosphatidylcholine Analogous Moieties", Macromolecular Rapid Communication, vol. 6, pp. 721-726 (1985).
International Search Report and Written Opinion from corresponding PCT Application No. PCT/GB2012/000542, 11 pages, (dated Oct. 10, 2010).

* cited by examiner

BIOCOMPATIBLE, BIOMIMETIC AMPHOLYTE MATERIALS

CROSS-REFERENCE TO RELATED APPLICATIONS

This patent application is a continuation of U.S. Ser. No. 13/529,708 filed Jun. 21, 2012 which claims priority to provisional patent application U.S. 61/500,921 filed Jun. 24, 2011, which is hereby incorporated by reference herein.

TECHNICAL FIELD

The Technical Field relates to an ampholyte compound and materials containing the same, as well as articles made with, or coated with, the same.

BACKGROUND

In recent years, biomimetic materials have been widely used as hydrophilic polymers employed in contact lenses, in intraocular lenses, as artificial organs and as haemocompatible coatings in blood contacting devices. Examples of natural hydrophilic polymers include collagen, alginates, hyaluronic acid, fibrin, and chitosan. The mentioned polymers have some degree of biocompatibility but often display poor mechanical strength. Examples of artificially synthesized polymers include polyesters, polyethers, polycarbonates, polyurethanes, polyacrylamides, and polyhydroxyethyl methacrylates. Although these polymers have high mechanical strength, low degradability and are easy to process, they present problems of biocompatibility for use in the field of medical devices.

SUMMARY OF THE INVENTION

Novel ampholyte compounds mimicking one of the major components present in membranes of natural cell such as 2-((2-hydroxyethyl)dimethylammonio)ethyl hydrogen phosphate have been synthesized and used to form synthetic polymeric ampholyte biomaterials using the methods described herein. The ampholyte polymeric biomaterials formed unexpectedly exhibit exceptional biocompatible properties such as high biocompatibility, haemocompatibility, and hydrophilicity. Additional functionalities are introduced to the ampholyte compounds to reach desired properties such as improved hydrophilicity, biocompatibility, non-thrombogenicity, anti-bacterial ability, mechanical strength, or suitability for a drug delivery platform. The ampholyte compounds can be polymerized with a variety of vinyl monomers or can be integrated or grafted into a polymeric backbone such as polyethers, polycarbonates, polymethacrylates, polyesters, polysiloxanes, polyacrylamides, or polyurethanes. Integration of the ampholyte compounds with and without additional functionalities in the polymeric backbone introduces desired properties such as hydrophilicity, non-thrombogenicity, anti-bacterial properties, appropriate mechanical strength, and suitability for drug delivery platform. The synthetic polymeric ampholyte biomaterials can be used to form medical devices or can be used to coat medical devices to improve the biocompatibility of the devices.

Embodiments include the materials of any of Formulas 1-16 as well as materials made from the same, including various devices, as well as polymers and copolymers made with other monomers. Embodiments include articles of manufacture and medical devices that are at least partially coated, or entirely coated, with one or more of the materials. These embodiments are set forth in detail below in the specification including in the claims.

DETAILED DESCRIPTION OF PREFERRED EMBODIMENTS

Ampholyte compounds are described herein that can be integrated or grafted into polymeric assemblies to give enhanced biocompatibility, wettability, drug delivery, and a range of different properties depending on the functional groups attached onto the ampholyte material. The ampholyte compounds are formed in good yield with reduced synthesis time. In some embodiments, microwave equipment is used to facilitate the synthesis. Polymeric materials comprising ampholyte compounds described herein can be used to make or coat a range of medical devices, e.g., to form contact lenses and intraocular lenses displaying high water content, flexibility, protein adsorption reduction, and tissue compatibility. The coating of the medical device with the polymeric assemblies described herein can be accomplished through physical adsorption or through covalent crosslinking of the polymer with functional groups present on the surface of the medical device in general. In some embodiments, it may be desirable to polymerize the ampholyte compounds described herein with the material of the medical device directly. In other embodiments, the copolymers can be dissolved in solution to be coated onto medical devices using dip-coating, spray coating (ultrasonic, electrostatic, thermal), dip-coating with UV cure, or dip-coated and cross-linked with a polyfunctional cross-linker (e.g. polyaziridines, polyisocyanates).

Embodiments include polymers (a term including copolymers) comprising an ampholyte compound herein that are crosslinked with a polyfunctional crosslinker. A polyfunctional crosslinker, as that term is used herein, is a molecule that comprises a two or more reactive groups that will form a covalent bond with the polymer. Embodiments include polyfunctional crosslinkers having between 2 and 100 reactive groups; artisans will immediately appreciate that all ranges and values between the explicitly stated ranges are contemplated, for instance, between 3 and about 50 or from 5 to about 95. Examples include vinyls, epoxides, aldehydes, imines, isocyanates, benzophenones, aziridines, maleimides, diimides, carbodiimides, and succinimides. These functional groups may be provided on a polymer that comprises an ampholyte or on separate polyfunctional crosslinker molecules. For instance, the reactive groups may be placed on a backbone of polyethylene glycol, polyvinyl pyrrolidinone, polyacrylate, polymethylacrylate, or polyalkylene oxide. The crosslinker may be added to a solution of the polymer comprising ampholyte, or otherwise contacted with the polymer. Crosslinking will take place upon mixing or may be activated when desired, depending upon the particular chemistry involved. The polyfunctional crosslinker may be part of a melt or solution comprising the ampholyte polymer, or added before, or after, such a polymer is contacted with a surface.

An embodiment is an ampholyte compound represented by the general formula

General Formula 1A

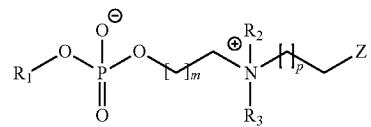

wherein $R_1$, $R_2$, and $R_3$ are independently chosen from the group consisting of
(a) an alkyl group,
(b) an aryl group,
(c) a cycloalkyl group,
(d) a cycloalkenyl group,
(e) a heterocycle group, and
(f) an alkenyl group,
wherein m and p independently range from 0 to 13, with an m of 1 to 13 denoting a hydrocarbon chain referred to as the m-hydrocarbon chain and a p in a range from 1 to 13 denoting a hydrocarbon chain referred to as the p-hydrocarbon chain and
wherein Z represents
(a) a carbon with a double bond to the compound or
(b) a group represented by a general formula of

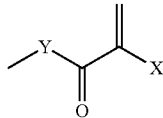

wherein X represents a hydrogen or a methyl, and Y represents an oxygen in an ester moiety or a secondary amine in an amide moiety.

In an alternative embodiment, Z represents a functional group for further covalent attachment to a polymer or other moiety. Examples of such functional groups are electrophiles or nucleophiles, for example, primary amine, hydroxyl, thiol, carboxyl, epoxides, aldehydes, imines, isocyanates, benzophenones, aziridines, maleimides, diimides, carbodiimides, succinimides, and carbodiimide. The choice of these or other functional groups will depend on the polymer that is to receive the ampholyte compound. Accordingly, a polymer comprising a plurality of functional groups may be decorated with a plurality of pendant ampholyte groups by a reaction between first functional groups on the polymer backbone and second functional groups on the ampholytes. In certain embodiments the first functional group and second functional groups are selected so as to undergo an electrophile-nucleophile covalent reaction.

Another embodiment is the ampholyte compound represented by the general formula 1A with the Z group as indicated therein having the Y group chosen as O, as follows:

General formula 1B

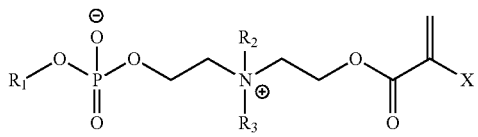

wherein $R_1$, $R_2$, and $R_3$ represent any one of the following:
(a) a substituted or unsubstituted alkyl
(b) a substituted or unsubstituted aryl
(c) a substituted or unsubstituted cycloalkyl
(d) a substituted or unsubstituted cycloalkenyl
(e) a substituted or unsubstituted heterocycle
(f) a substituted or unsubstituted alkenyl, and
wherein X represents a hydrogen or methyl.

In another embodiment, the ampholyte compound described herein is represented by the general formula:

General formula 1C

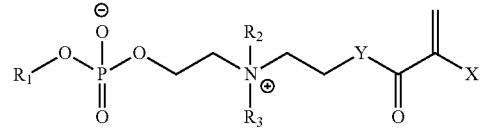

wherein $R_1$, $R_2$, and $R_3$ represent any one of the following:
(a) a substituted or unsubstituted alkyl
(b) a substituted or unsubstituted aryl
(c) a substituted or unsubstituted cycloalkyl
(d) a substituted or unsubstituted cycloalkenyl
(e) a substituted or unsubstituted heterocycle
(f) a substituted or unsubstituted alkenyl, and
wherein X represents a hydrogen or methyl and Y represents an oxygen to give an ester moiety or a secondary amine to give an amide moiety.

The ampholytes of general formulas 1A, 1B, and 1C may be polymerized with or without other monomers and with or without crosslinkers. The ampholytes may also be grafted onto existing polymers.

Accordingly, another embodiment is directed to a compound comprising a polymer that comprises an ampholyte compound pendant group, with said polymer and ampholyte pendant group being represented by the formula General formula 2A

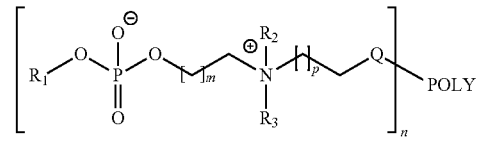

or the formula:

General formula 2B

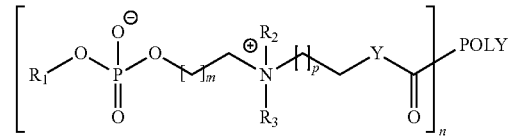

wherein POLY represents a polymer backbone,
wherein Q (in general formula 2A) represents a linker to the polymer backbone,
wherein Y (in general formula 2B) represents an oxygen in an ester moiety or a secondary amine in an amide moiety.
wherein m and p independently range from 0 to 13, with an m of 1 to 13 denoting a hydrocarbon chain referred to as the m-hydrocarbon chain and a p in a range from 1 to 13 denoting a hydrocarbon chain referred to as the p-hydrocarbon chain and
wherein $R_1$, $R_2$, and $R_3$ are independently chosen from the group consisting of
(a) an alkyl group,
(b) an aryl group, (c) a cycloalkyl group, (d) a cycloalkenyl group, (e) a heterocycle group, and (f) an alkenyl group.

The symbol n represents a number of pendant groups, each of which are independently chosen and attached to the polymer backbone. As is evident, the various pendant groups will be independently attached to the polymer backbone so that the polymer will comprise the polymer backbone and a plurality of the pendant groups. Further, other pendant groups may be attached to the polymer, or the polymer may be free of pendant groups besides those depicted in the general formula. The polymer, or the polymer backbone, may range in weight from, for instance, 100 to 10,000,000 Daltons. The amount of the ampholyte pendant group may be freely varied, for instance, from about 0.1% to about 99% w/w of the total compound that comprises the pendant group; artisans will immediately recognize that all numbers and ranges within the explicitly stated bounds are contemplated, e.g, about 2% w/w from about 5% to about 50% w/w. These ranges are generally applicable to the embodiments of general formulas 1-16 or polymers made therefrom. To achieve these ranges, for instance, the ampholyte compound may be polymerized from a concentrated state, or mixed with various other monomers for polymerization. Or a polymer may be selected to serve as the polymer backbone and lightly or heavily decorated with ampholyte pendant groups, as well as other pendant groups.

The symbol Q represents a linker, with a variety of chemical options existing for making the linkage. For instance, Q may be chosen from the group consisting of a substituted or unsubstituted hydrocarbon chain ranging from 1 to 13 carbons, a substituted or unsubstituted alkyl, a substituted or unsubstituted aryl, a substituted or unsubstituted cycloalkyl, a substituted or unsubstituted cycloalkenyl, a substituted or unsubstituted heterocycle, a substituted or unsubstituted alkenyl, a functional chain comprising an ester, a functional chain comprising an amide, a functional chain comprising a urea, a functional chain comprising a carbonate, a functional chain comprising a carbamate, a functional chain comprising a poly(ethylene oxide), and a functional chain comprising a poly(propylene) oxide polymer.

In one embodiment, a polymer grafted with an ampholyte compound described herein is represented by the general formula:

General formula 2C

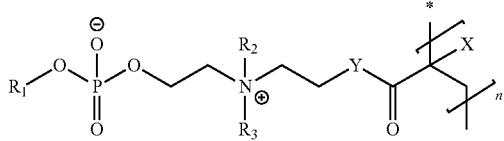

wherein X represents a hydrogen or methyl, Y represents an oxygen to give an ester moiety or a secondary amine to give an amide moiety, and $R_1$, $R_2$, and $R_3$ are independently chosen as above to be (a) to (f).

In another embodiment, the ampholyte compound described herein is represented by the general formula:

General formula 3A

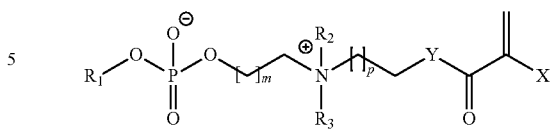

wherein X represents a hydrogen or methyl, Y represents an oxygen to give an ester moiety or a secondary amine to give an amide moiety, and $R_1$, $R_2$, and $R_3$ are independently chosen as above to be (a) to (f), and wherein m and p represent substituted or unsubstituted hydrocarbon chain, with number of carbons ranging from 0 to 13.

The corresponding polymer grafted with the ampholyte compound of general formula 3A is represented by the general formula:

General formula 3B

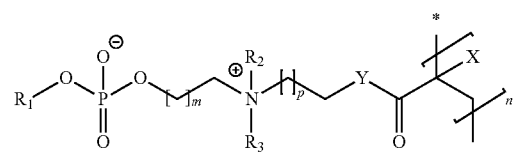

wherein X represents a hydrogen or methyl, Y represents an oxygen to give an ester moiety or a secondary amine to give an amide moiety, and $R_1$, $R_2$, and $R_3$ are independently chosen as above to be (a) to (f), and wherein m and p represent substituted or unsubstituted hydrocarbon chain, with number of carbons ranging from 0 to 13.

An embodiment is a polymer comprising a polymerization product of an ampholyte monomer represented by a general formula:

General Formula 4A

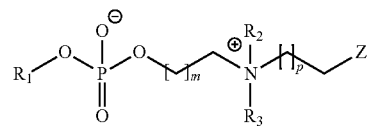

wherein $R_1$, $R_2$, and $R_3$, are independently chosen from the group consisting of (a) an alkyl group, (b) an aryl group, (c) a cycloalkyl group, (d) a cycloalkenyl group, (e) a heterocycle group, and (f) an alkenyl group;

wherein m and p independently range from 0 to 13, with an m of 1 to 13 denoting a hydrocarbon chain referred to as the m-hydrocarbon chain and a p in a range from 1 to 13 denoting a hydrocarbon chain referred to as the p-hydrocarbon chain; and wherein Z represents a polymerizable group comprising a vinylic or allylic group that is capable of undergoing free radical polymerization.

Free radical polymerization is, in general, accomplished with a vinylic or allylic group. The monomer of Formula 4A may be polymerized by itself or with comonomers that also undergo free radical polymerization. Examples of comonomers include one or more of: acrylates, methacrylates, 2-hydroxyethyl methacrylate, hydroxypropyl methacrylate, n-butyl methacrylate, tert-butyl methacrylate, n-hexyl methacrylate, 2-methoxyethyl methacrylate, poly(hexanide) methacrylate, poly(hexanide) polyethylene oxide methacrylate, or alkyl derivatized poly(hexanide) methacrylate, heparin derivatized polyethylene oxide macromer, vinyl sulfonic acid monomer, monomers comprising poly(ethylene glycol), N-vinyl pyrrolidone monomers, 4-benzoylphenyl methacrylate allyl methyl carbonate, allyl alcohol, allyl isocyanate, methacryloyloxyethyl phosphorylcholine.

Various monomers (a term used herein as including macromers) are disclosed in U.S. Pat. Nos. 6,127,348, 6,121,027, PCT GB9701173, U.S. Pat. Nos. 6,096,798, 6,060,582, 5,993,890; 5,945,457; 5,877,263; 5,855,618; 5,846,530; 5,837,747; 5,783,570; 5,776,184; 5,763,504; 5,741,881; 5,741,551; 5,728,751; 5,583,213; 5,512,329; 5,462,976; 5,344,455; 5,183,872; 4,987,181; 4,331,697; 4,239,664; 4,082,727; US Pub 2003/0021762, and European patents 049,828 A1 & B1. These references are incorporated herein by reference for all purposes, including use of the monomers as comonomers or making polymers for decoration with an ampholyte compound.

The monomer of Formula 4A may be polymerized with one or more comonomers having a general formula: R'Y'(CO)C=CX' (Formula 4B) wherein X' represents a hydrogen or a methyl, Y' represents an oxygen in an ester moiety or a secondary amine in an amide moiety, and R' represents a member of the group chosen from (a) an alkyl group, (b) an aryl group, (c) a cycloalkyl group, (d) a cycloalkenyl group, (e) a heterocycle group, and (f) an alkenyl group. For instance, the monomers of Formula 4A and 4B may be further polymerized with a monomer of formula R"Y"(CO)C=CX" (Formula 4C) wherein X" represents a hydrogen or a methyl, Y" represents an oxygen in an ester moiety or a secondary amine in an amide moiety, and R" represents a member of the group chosen from (a) an alkyl group, (b) an aryl group, (c) a cycloalkyl group, (d) a cycloalkenyl group, (e) a heterocycle group, and (f) an alkenyl group.

The monomer of Formula 4A may be polymerized with a monomer of general formula: $R^{iv}$C=CX (Formula 4D) wherein X represents a hydrogen or a methyl, and wherein $R^{iv}$ is chosen from the group consisting of (a) an alkyl group, (b) an aryl group, (c) a cycloalkyl group, (d) a cycloalkenyl group, (e) a heterocycle group, (f) an alkenyl group, and (g) a alkyl tertiary amine group.

In one embodiment, a copolymer grafted with ampholyte compound described herein is represented by the general formula:

General formula 5

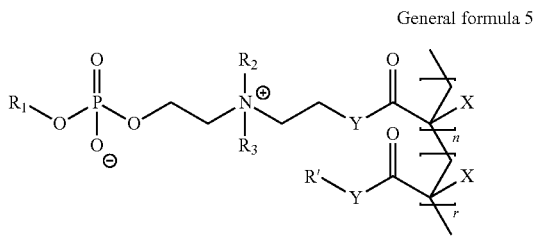

wherein X represents a hydrogen or methyl, Y represents an oxygen to give an ester moiety or a secondary amine to give an amide moiety, and $R_1$, $R_2$, and $R_3$ as above (a) to (f), wherein R' represents any one of the following:
(g) a substituted or unsubstituted alkyl
(h) a substituted or unsubstituted aryl
(i) a substituted or unsubstituted cycloalkyl
(j) a substituted or unsubstituted cycloalkenyl
(k) a substituted or unsubstituted heterocycle
(l) a substituted or unsubstituted alkenyl, and
wherein n and r represent the number of units of each monomer.

In another embodiment, a copolymer grafted with the ampholyte compound described herein is represented by the general formula:

General formula 6

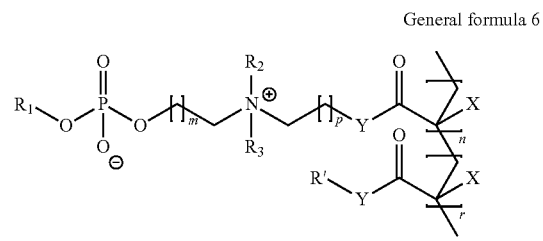

wherein X represents a hydrogen or methyl, Y represents an oxygen to give an ester moiety or a secondary amine to give an amide moiety, $R_1$, $R_2$, and $R_3$ as above (a) to (f), and R' as above (g) to (l), wherein m and p represent substituted or unsubstituted hydrocarbon chain, with number of carbons ranging from 0 to 13, and wherein n and r represent the number of units of each monomer.

In yet another embodiment, a copolymer grafted with ampholyte compound described herein is represented by the general formula:

General formula 7

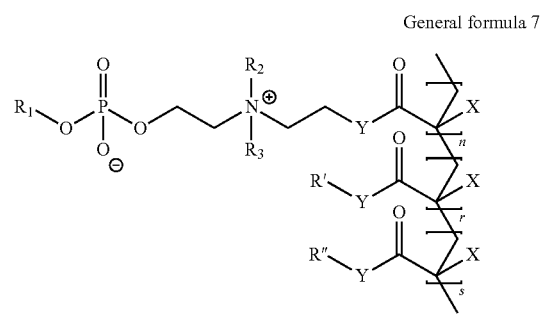

wherein X represents a hydrogen or methyl, Y represents an oxygen to give an ester moiety or a secondary amine to give an amide moiety, $R_1$, $R_2$, and $R_3$ as above (a) to (f), and R' as above (g) to (l), wherein R" represents any one of the following:
(t) a substituted or unsubstituted alkyl
(u) a substituted or unsubstituted aryl
(v) a substituted or unsubstituted cycloalkyl
(w) a substituted or unsubstituted cycloalkenyl
(y) a substituted or unsubstituted heterocycle
(z) a substituted or unsubstituted alkenyl, and
wherein n, r and s represent the number of units of each monomer.

In one embodiment, a copolymer grafted with ampholyte compound described herein is represented by the general formula:

General formula 8

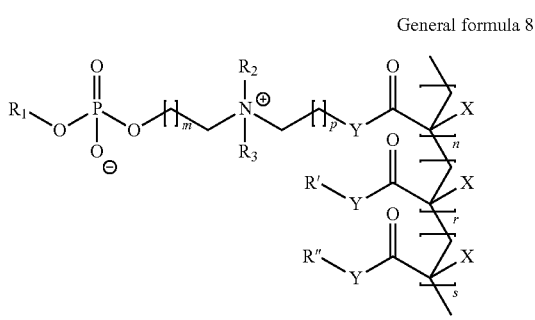

wherein X represents a hydrogen or methyl, Y represents an oxygen to give an ester moiety or a secondary amine to give an amide moiety, $R_1$, $R_2$, and $R_3$ as above (a) to (f), R' as above (g) to (l), and R" as above (t) to (z), wherein m and p represent substituted or unsubstituted hydrocarbon chain, with number of carbons ranging from 0 to 13, and wherein n, r, and s represent the number of units of each monomer.

In one embodiment, a copolymer grafted with ampholyte compound described herein is represented by the general formula:

General formula 9

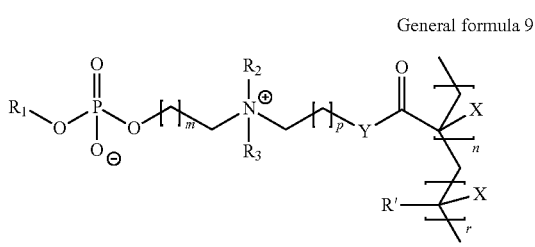

wherein X represents a hydrogen or methyl, Y represents an oxygen to give an ester moiety or a secondary amine to give an amide moiety, $R_1$, $R_2$, and $R_3$ as above (a) to (f), and R' as above (g) to (l), wherein m and p represent substituted or unsubstituted hydrocarbon chain, with number of carbons ranging from 0 to 13, and wherein n and r represent the number of units of each monomer.

In one embodiment, a copolymer grafted with the ampholyte compound described herein is represented by the general formula:

General formula 10

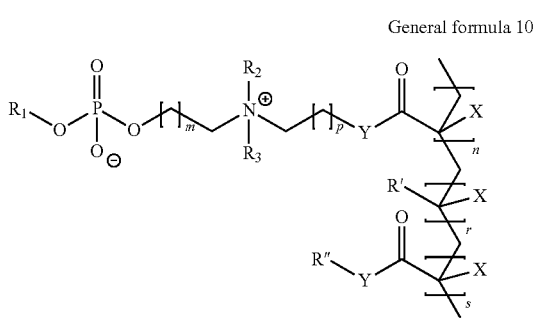

wherein X represents a hydrogen or methyl, Y represents an oxygen to give an ester moiety or a secondary amine to give an amide moiety, $R_1$, $R_2$, and $R_3$ as above (a) to (f), R' as above (g) to (l), and R" as above (t) to (z), wherein m and p represent substituted or unsubstituted hydrocarbon chain, with number of carbons ranging from 0 to 13, and wherein n, r, and s represent the number of units of each monomer.

In one embodiment, a copolymer grafted with the ampholyte compound described herein is represented by the general formula:

General formula 11

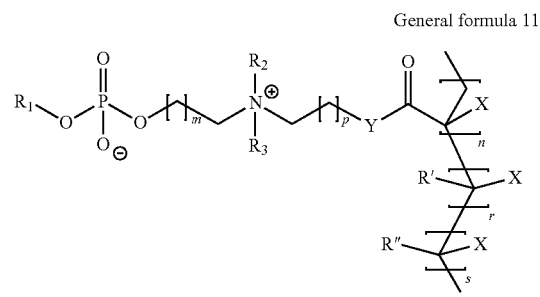

wherein X represents a hydrogen or methyl, Y represents an oxygen to give an ester moiety or a secondary amine to give an amide moiety, $R_1$, $R_2$, and $R_3$ as above (a) to (f), R' as above (g) to (l), and R" as above (t) to (z), wherein m and p represent substituted or unsubstituted hydrocarbon chain, with number of carbons ranging from 0 to 13, and wherein n, r, and s represent the number of units of each monomer.

In one embodiment, the copolymer described herein is represented by the general formula General Formula 12

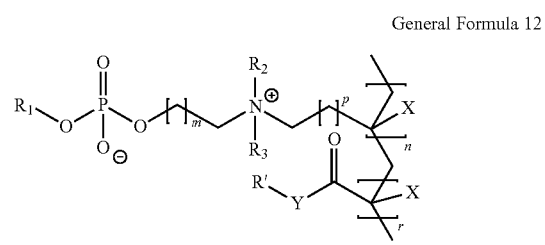

wherein X, Y, $R_1$, $R_2$, $R_3$, and R' represent the functional groups or atoms as above and m, p, n and r represent the number of units or number of atoms as above.

In another embodiment, the copolymer describe herein is represented by the general formula General Formula 13

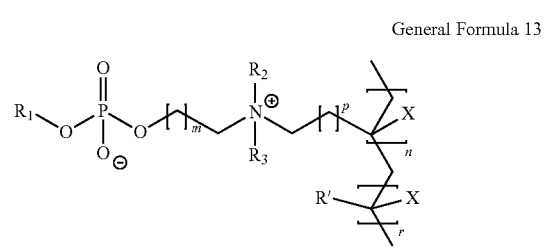

wherein X, Y, $R_1$, $R_2$, and $R_3$ and R' represent the functional groups or atoms as above and m, p, n and r represent the number of units or number of atoms as above.

In yet another embodiment, the copolymer described herein is represented by the general formula General Formula 14

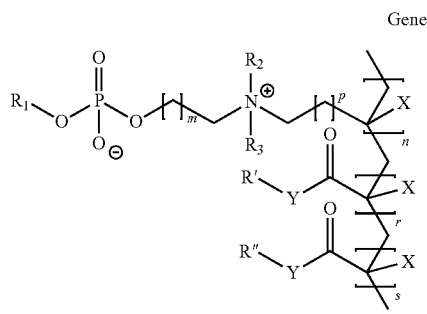

wherein X, Y, $R_1$, $R_2$, $R_3$, R' and R" represent the functional groups or atoms as above and m, p, n, r and s represent the number of units or number of atoms as above.

In one embodiment, the copolymer described herein is represented by the general formula General Formula 15

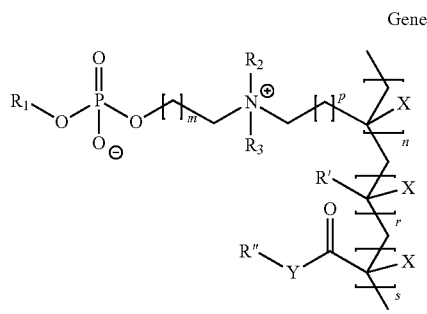

wherein X, Y, $R_1$, $R_2$, $R_3$, R' and R" represent the functional groups or atoms as above and m, p, n, r and s represent the number of units or number of atoms as above.

In another embodiment, the copolymer described herein is represented by the general formula General Formula 16

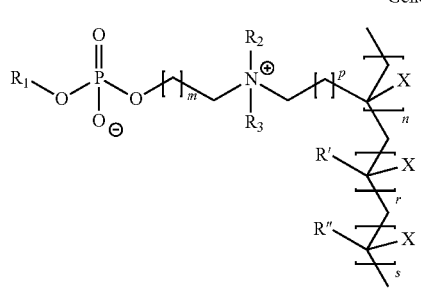

wherein X, Y, $R_1$, $R_2$, $R_3$, R' and R" represent the functional groups or atoms as above and m, p, n, r and s represent the number of units or number of atoms as above.

The term ampholyte is used herein to describe compounds having zwitterion moiety. The term group refers to a chemical moiety that may comprise one or more additional groups. In general formulas 1-16, X can be any group attached to a polymerizable moiety including hydrogen, or methyl. Although X is used to represent side groups in the polymer, it is understood that X can be different in the same formula, with the X being chosen independently for each monomer group. The term substituted or unsubstituted is used to describe chemical functional group that may be itself substituted with one or more additional substitute groups. These additional substitute groups can include hetero atoms such as O, N, or S. However the number, substitution position and type of bonded substituent are not specifically limited unless specifically stated. $R_1$, $R_2$, and $R_3$, each independently represents a substituted or unsubstituted alkyl, a substituted or unsubstituted aryl group, a substituted or unsubstituted cycloalkyl group, a substituted or unsubstituted cycloalkenyl group, a substituted or unsubstituted heterocycle group or a substituted or unsubstituted alkenyl group. R' represents a substituted or unsubstituted alkyl group or a substituted or unsubstituted aryl group or a substituted or unsubstituted cycloalkyl group or a substituted or unsubstituted cycloalkenyl group or a substituted or unsubstituted heterocycle group or a substituted or unsubstituted alkenyl group. R" represents a substituted or unsubstituted alkyl group or a substituted or unsubstituted aryl group or a substituted or unsubstituted cycloalkyl group or a substituted or unsubstituted cycloalkenyl group or a substituted or unsubstituted heterocycle group or a substituted or unsubstituted alkenyl group. In general formula 1-16, m and p represents the number of carbon in the hydrocarbon chain with values ranging from 0 to 13 where the hydrocarbon chain may or may not be substituted. In general formula 1-16, n, r and s represent the number of units of each monomer in the copolymer backbone and can be any reasonable number known in the art. In some embodiments, the number of monomers n, r, or s is in the range between 10 to 1,000,000 repeating units. The monomer numbers n, r, and s may be the same or different in the same formula. Co-monomers may be used with the ampholyte compounds disclosed herein. Examples of co-monomers include acrylates, methacrylates (for example 2-hydroxyethyl methacrylate, hydroxypropyl methacrylate, n-butyl methacrylate, tert-butyl methacrylate, n-hexyl methacrylate, 2-methoxyethyl methacrylate, poly (hexanide) methacrylate, poly(hexanide) polyethylene oxide methacrylate, or alkyl derivatized poly(hexanide) methacrylate), heparin derivatized polyethylene oxide, vinyl sulfonic acid, poly(ethylene glycol), N-vinyl pyrrolidone, and 4-benzoylphenyl methacrylate.

A general method of synthesis is exemplified by the following schemes. The compounds made in Examples 1-3 follow Scheme I. The compounds made in Example 4 follows Scheme II. The schemes may be modified to produce the embodiments of ampholyte compounds set forth in General Formulas 1A, 1B, and 1C.

Scheme I

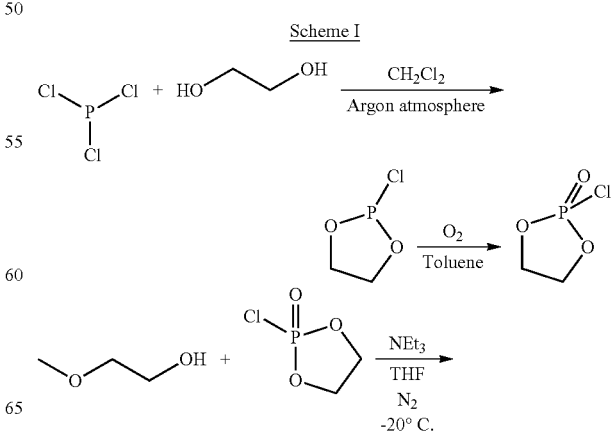

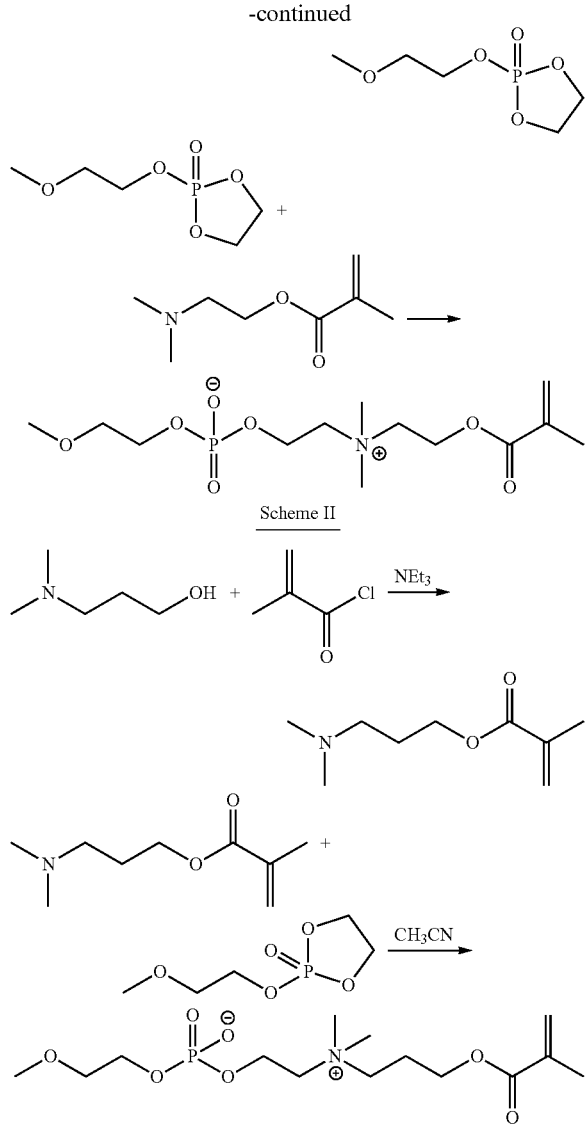

Examples 5-8 detail the polymerization of various ampholyte-containing materials and polymers. 2-((2-(methacryloyloxy)ethyl) dimethylammonio)ethyl 2-methoxyethyl phosphate) was copolymerised with n-butyl methacrylate in various concentrations and conditions in Examples 5-7. 2 ((3 (methacryloyloxy)propyl)dimethylammonio)ethyl 2-methoxyethyl phosphate was polymerized with n-butyl methacrylate in Example 8. 2-((2-(methacryloyloxy)ethyl) dimethylammonio)ethyl 2-methoxyethyl phosphate from Example 3 was copolymerized with hexyl methacrylate (30% mol) and methoxyethyl methacrylate in Example 9. 2-((2-(methacryloyloxy)ethyl)dimethylammonio)ethyl 2-methoxyethyl phosphate from Example 3 (30% mol) was copolymerized with hexyl methacrylate and methoxyethyl methacrylate in Example 10. 2-((2-(methacryloyloxy)ethyl) dimethylammonio)ethyl 2-methoxyethyl phosphate from Example 3 was copolymerized in varying conditions with hexyl methacrylate and hydroxypropyl methacrylate in Examples 11 and 12. Example 13 describes an embodiment of a contact lens material comprising an ampholyte compound as described herein. All of these polymers were made so as to demonstrate the properties of the ampholyte compound in a variety of conditions.

Examples 14-18 detail testing of the ampholyte-containing materials. Table 1 in Example 16 summarizes the improved haemocompatible properties of the ampholyte-containing materials compared to an uncoated polystyrene represented by significantly reduced numbers of platelets and aggregates. Tables 2A and 2B in Example 17 summarize results showing the ampholyte-containing materials adsorbed less protein compared to relevant control materials. The reduced protein adsorption points to a basis for improved biocompatibility of the materials. The reduced adsorption was observed across a range of copolymers and a range of copolymerization conditions, demonstrating a correlation between presence of the ampholyte and improved biocompatibility. Example 18 exposed a variety of the ampholyte-containing materials to cells and demonstrated that cellular adhesion was very low or non-existent, which further demonstrated a correlation between presence of the ampholyte and improvements in biocompatibility.

One use of the ampholyte-containing polymers is in the medical arts, with medical devices being made from, containing at least some, or being at least partially coated with, an ampholyte-containing polymer. The devices may be, for example, blood-contacting devices, implantable devices, fully implanted devices (meaning no portion of the device is left outside the body), partially implanted devices (meaning a portion of the device is inside a patient and a portion is exterior to the patient), devices that contact a patient's blood or bodily fluid, catheters, blood-contacting lines (cardiac devices, heart-lung machines, dialysis lines), dialysis machines, dialysis membranes. Examples of fully implantable devices are artificial blood vessels, stents (cardiac, venous, arterial, kidney, ureter), valves (cardiac, venous, arterial), cardiac valve leaflets, shunts, cardiac devices (pacemakers, defibrillators). Examples of partially implanted devices are transcutaneous catheters, dialysis ports, ports for chemotherapy. Devices made entirely of, or at least partially of, the ampholyte-containing polymers are, for example, contact lenses, intraocular lenses, catheters, and biomedical valves.

A medical device or other article of manufacture may be made from, or at least partially coated with, the ampholyte, a polymer comprising the ampholyte, or a coating material that comprises the ampholyte and/or polymer containing the ampholyte. The ampholyte, coating material, or polymer comprising the ampholyte may be adsorbed to the surface, covalently attached to the surface, or the surface material may be at least partially made of the polymer and/or ampholyte. Methods include, for instance, those wherein the ampholyte-containing compound is dissolved in solution and coated onto the medical device using dip-coating, spray coating, ultrasonic spray coating, electrostatic spray coating, thermal spray coating, dip-coating with UV cure, or dip-coated and cross-linked with a polyfunctional cross-linker. The coating may be free of covalent cross-links. Alternatively, crosslinkers may be placed into the coating. Embodiments include coatings and/or materials wherein the compound is covalently crosslinked with a polyfunctional cross-linker that comprises a polyaziridine, a polyisocyanate, a polycarbodiimide, or a combination thereof.

EXAMPLES

Certain embodiments of the invention are described in greater detail below through examples.

Example 1

Synthesis of 2-((2-(methacryloyloxy)ethyl)dimethylammonio)ethyl 2-methoxyethyl Phosphate using SCHOTT Duran Pressure Bottle The first two steps to provide 2-chloro-1,3,2-dioxaphospholane oxide were previously described and carried out according to the methods of Lucas and Edmundson.

Freshly distilled 2-methoxyethanol was blended in an oven-dried round bottom flask, flushed with nitrogen, with anhydrous tetrahydrofuran and freshly distilled triethylamine. The mixture was stirred under $N_2$ for 10 min and cooled down to −20° C. A solution of 2-chloro-1,3,2-dioxaphospholane oxide in anhydrous tetrahydrofuran was added slowly at −20° C. over a period of 20 min. Once the addition was finished, the mixture was stirred a further 2 hours at −10/−20° C., followed by 2 hours at 0/5° C. and slowly allowed to warm up to room temperature over 1 hour. The precipitate of triethylamine hydrochloride was filtered through celite and glass wool, and THF was removed by distillation. The intermediate product was finally dried under vacuum for 30 minutes to remove excess triethylamine and obtain the intermediate oil of methoxyethyl-1,3,2-dioxaphospholane oxide (81%).

The intermediate oil was blended in an oven-dried glass bottle (SCHOTT Duran 100 mL) with freshly distilled 2-(dimethylamino)ethyl methacrylate (Aldrich) (1 equivalent) and 2000 ppm of 2-methoxyphenol (Aldrich) with freshly distilled acetonitrile (0.3 molar). The mixture was stirred at 60° C. for 42 hours. At the completion of the reaction, most of the acetonitrile was removed in a stream of nitrogen. The remaining yellow/brown oil was dissolved in a minimum amount of anhydrous methanol and reprecipitated from anhydrous diethyl ether. This process was repeated 3 times. The crude oil was purified by silica gel column chromatography using a mixture of acetonitrile/methanol/water in a ratio of 4/1/1, respectively, yielding a transparent viscous oil. The oil was completely dried from water when dissolved in a small amount of acetonitrile and dried over $MgSO_4$ for 1 hour. The compound was dried under a stream of $N_2$ and finally under high vacuum (yield=9%).

$^1$H NMR (400 MHz, $D_2O$) δ ppm: 1.85 (s, 3H, $CH_3$—C=$CH_2$—), 3.19 (s, 6H, $CH_3$—$N^+$—$CH_3$), 3.31 (s, 3H, $CH_3$—O—), 3.56 to 3.59 (m, 2H, —$CH_2$—O—), 3.68 to 3.71 (m, 2H, —$CH_2$—$N^+$—), 3.77 to 3.82 (m, 2H, —$CH_2$—$N^+$—), 3.91 to 3.95 (m, 2H, —$CH_2$—O—P=O), 4.25 (br. s, 2H, —$CH_2$—O—P=O), 4.57 (br. s, 2H, —$CH_2$—O—C=O), 5.69 (d, J=4, 1H, $CH_2$=C—) and 6.07 (d, J=4, 1H, $CH_2$=C—); $^{31}$P NMR (162 MHz, $D_2O$) δ ppm: −0.34; $^{13}$C NMR (100 MHz, $D_2O$) δ ppm: 17.23 ($CH_3$—C=$CH_2$—), 52.14 ($CH_3$—$N^+$—$CH_3$), 58.07 ($CH_3$—O—$CH_2$—), 58.40 (—$CH_2$—O—C=O), 59.12 (—$CH_2$—O—P=O), 63.60 ($CH_2$—$N^+$—$CH_2$), 64.70 and 64.76 ($CH_2$—$N^+$—$CH_2$ and —$CH_2$—O—P=O), 71.38 ($CH_3$—O—$CH_2$—), 127.67 ($CH_2$=C—), 135.11 ($CH_2$=C—$CH_3$), 168.36 (O—C=O); FT-IR $v_{max}$/cm$^{-1}$: 1718 (O—C=O st.), 1637 (C=C st.), 1456 (—$N^+(CH_3)_2$ def.), 1320 ($CH_3$ def.), 1296 (P=O st.), 1217 (C—O—C st.), 1158 (C—N bend), 1042 (P—O—C st.), 949 (—$N(CH_3)_2$ st.), 842 ($CH_2$), 789 ($CH_2$); ESI LCMS for $C_{13}H_{27}O_7NP$ found m/z 340.1520 [M+H]$^+$ (calculated 340.1525) and $C_{13}H_{26}O_7NPNa$ found 362.1338 m/z [M+Na]$^+$ (calculated 362.1345).

Example 2

Synthesis of 2-((2-(methacryloyloxy)ethyl)dimethylammonio)ethyl 2-methoxyethyl Phosphate using SCHOTT Duran Pressure Bottle and Increased Concentration of Reagents in Solvent The first two steps to provide 2-chloro-1,3,2-dioxaphospholane oxide were previously described and carried out according to the methods of Lucas[7] and Edmundson[8].

Methoxyethyl-1,3,2-dioxaphospholane oxide was prepared as described in Example 1. The methoxyethyl-1,3,2-dioxaphospholane oxide (1 equivalent) was blended in an oven-dried glass bottle (SCHOTT Duran 100 mL) with freshly distilled 2-(dimethylamino)ethyl methacrylate (Aldrich) (1 equivalent) and 2000 ppm of 2-methoxyphenol (Aldrich) with freshly distilled acetonitrile (2 molar). The mixture was stirred at 120° C. for 24 hours. At the completion of the reaction, most of the acetonitrile was removed in a stream of nitrogen. The remaining yellow/brown oil was dissolved in a minimum amount of anhydrous methanol and reprecipitated from anhydrous diethyl ether. This process was repeated 3 times. The crude oil was purified by silica gel column chromatography using a mixture of acetonitrile/methanol/water in a ratio of 4/1/1, respectively, yielding a transparent viscous oil. The oil was completely dried from water when dissolved in a small amount of acetonitrile and dried over $MgSO_4$ for 1 hour. The compound was dried under a stream of $N_2$ and finally under high vacuum (yield=65%).

$^1$H NMR (400 MHz, $D_2O$) δ ppm: 1.85 (s, 3H, $CH_3$—C=$CH_2$—), 3.19 (s, 6H, $CH_3$—$N^+$—$CH_3$), 3.31 (s, 3H, $CH_3$—O—), 3.56 to 3.59 (m, 2H, —$CH_2$—O—), 3.68 to 3.71 (m, 2H, —$CH_2$—$N^+$—), 3.77 to 3.82 (m, 2H, —$CH_2$—$N^+$—), 3.91 to 3.95 (m, 2H, —$CH_2$—O—P=O), 4.25 (br. s, 2H, —$CH_2$—O—P=O), 4.57 (br. s, 2H, —$CH_2$—O—C=O), 5.69 (d, J=4, 1H, $CH_2$=C—) and 6.07 (d, J=4, 1H, $CH_2$=C—); $^{31}$P NMR (162 MHz, $D_2O$) δ ppm: −0.34; $^{13}$C NMR (100 MHz, $D_2O$) δ ppm: 17.23 ($CH_3$—C=$CH_2$—), 52.14 ($CH_3$—$N^+$—$CH_3$), 58.07 ($CH_3$—O—$CH_2$—), 58.40 (—$CH_2$—O—C=O), 59.12 (—$CH_2$—O—P=O), 63.60 ($CH_2$—$N^+$—$CH_2$), 64.70 and 64.76 ($CH_2$—$N^+$—$CH_2$ and —$CH_2$—O—P=O), 71.38 ($CH_3$—O—$CH_2$—), 127.67 ($CH_2$=C—), 135.11 ($CH_2$=C—$CH_3$), 168.36 (O—C=O); FT-IR $v_{max}$/cm$^{-1}$: 1718 (O—C=O st.), 1637 (C=C st.), 1456 (—$N^+(CH_3)_2$ def.), 1320 ($CH_3$ def.), 1296 (P=O st.), 1217 (C—O—C st.), 1158 (C—N bend), 1042 (P—O—C st.), 949 (—$N(CH_3)_2$ st.), 842 ($CH_2$), 789 ($CH_2$); ESI LCMS for $C_{13}H_{27}O_7NP$ found m/z 340.1520 [M+H]$^+$ (calculated 340.1525) and $C_{13}H_{26}O_7NPNa$ found 362.1338 m/z [M+Na]$^+$ (calculated 362.1345).

Example 3

Synthesis of 2-((2-(methacryloyloxy)ethyl)dimethylammonio)ethyl 2-methoxyethyl Phosphate using Microwave Energy The first two steps to provide 2-chloro-1,3,2-dioxaphospholane oxide were previously described and carried out according to the methods of Lucas[7] and Edmundson[8].

Methoxyethyl-1,3,2-dioxaphospholane oxide was prepared as described in Example 1. The Methoxyethyl-1,3,2-dioxaphospholane oxide obtained (1 equivalent) was blended in an oven-dried microwave thick wall vessel with freshly distilled 2-(dimethylamino)ethyl methacrylate (Aldrich) (1 equivalent) and 2000 ppm of 2-methoxyphenol (Aldrich) with freshly distilled acetonitrile (2M). The reaction mixture was placed in a CEM Discover microwave, stirring at 125° C. for 4 hours with a power of 150 watts. At the completion of the reaction, most of the acetonitrile was removed in a stream of nitrogen. The remaining brown oil was dissolved in a minimum amount of anhydrous methanol and reprecipitated from anhydrous diethyl ether. This process was repeated 3 times. The crude oil was purified by silica gel column chromatography using a mixture of acetonitrile/methanol/water in a ratio of 4/1/1, respectively, yielding a transparent viscous oil. The oil was completely dried from water when dissolved in a small amount of acetonitrile and dried over $MgSO_4$ for 1 hour. The compound was dried under a stream of $N_2$ and finally under high vacuum (yield=73%).

$^1$H NMR (400 MHz, $D_2O$) δ ppm: 1.85 (s, 3H, $CH_3$—C=$CH_2$—), 3.19 (s, 6H, $CH_3$—$N^+$—$CH_3$), 3.31 (s, 3H, $CH_3$—O—), 3.56 to 3.59 (m, 2H, —$CH_2$—O—), 3.68 to 3.71 (m, 2H, —$CH_2$—$N^+$—), 3.77 to 3.82 (m, 2H, —$CH_2$—$N^+$—), 3.91 to 3.95 (m, 2H, —$CH_2$—O—P=O), 4.25 (br. s, 2H, —$CH_2$—O—P=O), 4.57 (br. s, 2H, —$CH_2$—O—C=O), 5.69 (d, J=4, 1H, $CH_2$=C—) and 6.07 (d, J=4, 1H, $CH_2$=C—); $^{31}$P NMR (162 MHz, $D_2O$) δ ppm: -0.34; $^{13}$C NMR (100 MHz, $D_2O$) δ ppm: 17.23 ($CH_3$—C=$CH_2$—), 52.14 ($CH_3$—$N^+$—$CH_3$), 58.07 ($CH_3$—O—$CH_2$—), 58.40 (—$CH_2$—O—C=O), 59.12 (—$CH_2$—O—P=O), 63.60 ($CH_2$—$N^+$—$CH_2$), 64.70 and 64.76 ($CH_2$—$N^+$—$CH_2$ and —$CH_2$—O—P=O), 71.38 ($CH_3$—O—$CH_2$—), 127.67 ($CH_2$=C—), 135.11 ($CH_2$=C—$CH_3$), 168.36 (O—C=O); FT-IR $v_{max}$/cm$^{-1}$: 1718 (O—C=O st.), 1637 (C=C st.), 1456 (—$N^+(CH_3)_2$ def.), 1320 ($CH_3$ def.), 1296 (P=O st.), 1217 (C—O—C st.), 1158 (C—N bend), 1042 (P—O—C st.), 949 (—$N(CH_3)_2$ st.), 842 ($CH_2$), 789 ($CH_2$); ESI LCMS for $C_{13}H_{27}O_7NP$ found m/z 340.1520 [M+H]$^+$ (calculated 340.1525) and $C_{13}H_{26}O_7NPNa$ found 362.1338 m/z [M+Na]$^+$ (calculated 362.1345).

Example 4

Synthesis of 2-((3-(methacryloyloxy)propyl)dimethylammonio)ethyl 2-methoxyethyl Phosphate The first two steps to provide 2-chloro-1,3,2-dioxaphospholane oxide were previously described and carried out according to the methods of Lucas[7] and Edmundson[8].

Methoxyethyl-1,3,2-dioxaphospholane oxide was prepared as described in Example 1. The 3-(dimethylamino) propyl methacrylate was synthesised according to the procedure described in Scheme II.

3-(dimethylamino) propanol (0.02 mol) was blended in an oven dried round bottom flask, flushed with $N_2$, with anhydrous diethyl ether (60 mL) and triethylamine (0.04 mol). The mixture was cooled down to -10° C. Methacryloyl chloride (0.02 mol) in 7 ml anhydrous diethyl ether was added dropwise to the reaction mixture over 30 min, maintaining the temperature at -10° C. under $N_2$. After the addition, the mixture was stirred and allowed to warm up slowly to room temperature overnight (20 h). The triethylammonium chloride salt was filtered through celite and glass wool and washed thoroughly with diethyl ether. The solvent was removed via rotary evaporation and the product was purified by distillation under reduced pressure (40° C. at 0.5 mm Hg) to afford a yield of 75%.

$^1$H NMR (400 MHz, $CDCl_3$) δ ppm: 1.85 (dt, J=8 and J=8, 2H, —$CH_2$—$CH_2$—$CH_2$—), 1.95 (s, 3H, $CH_3$—C=$CH_2$), 2.22 (s, 6H, —$N(CH_3)_2$), 2.36 (t, J=8, 2H, —N—$CH_2$—), 4.20 (t, J=8, 2H, —$CH_2$—O—C=O), 5.55 (d, J=4, 1H, $CH_2$=C—) and 6.10 (d, J=4, 1H, $CH_2$=C—); $^{13}$C NMR (100 MHz, $CDCl_3$) δ ppm: 18.30 ($CH_3$—C=$CH_2$—), 27.00 (—$CH_2$—$CH_2$—$CH_2$—), 45.47 ($CH_3$—N—$CH_3$), 56.30 ($CH_3$—N—($CH_3)_2$), 63.02 (—$CH_2$—O—C=O), 125.24 ($CH_2$=C—), 136.43 ($CH_2$=C—$CH_3$), 167.40 (O—C=O); FT-IR $v_{max}$/cm$^{-1}$: 2934 ($CH_3$, $CH_2$ st.), 1732 (O—C=O st.), 1677 (C=C st), 1154 (C—C—N bend), 1036 (C—O—C st.); ESI LCMS for $C_9H_{18}O_2N$ found m/z 172.1329 [M+H]$^+$ (calculated 172.1338).

The methoxyethyl-1,3,2-dioxapholane oxide obtained (1 equivalent) was blended in an oven-dried glass bottle (SCHOTT Duran 100 mL) with previously synthesised 3-(dimethylamino)propyl methacrylate (1 equivalent) and 2000 ppm of 2-methoxyphenol (Aldrich) with freshly distilled acetonitrile (2.6 molar). The mixture was stirred at 120° C. for 24 hours. At the completion of the reaction, most of the acetonitrile was removed in a stream of nitrogen. The remaining yellow/brown oil was dissolved in a minimum amount of anhydrous methanol and reprecipitated from anhydrous diethyl ether. This process was repeated 3 times. The crude oil was purified by silica gel column chromatography using a mixture of acetonitrile/methanol/water in a ratio of 4/1/1, respectively, yielding a transparent viscous oil. The oil was completely dried from water when dissolved in a small amount of acetonitrile and dried over $MgSO_4$ for 1 hour. The compound was dried under a stream of $N_2$ and finally under high vacuum (yield=46%).

$^1$H NMR (400 MHz, $D_2O$) δ ppm: 1.81 (s, 3H, $CH_3$—C=$CH_2$—), 2.11 to 2.18 (m, 2H, $CH_2$—$CH_2$—$CH_2$—), 3.08 (s, 6H, $CH_3$—$N^+$—$CH_3$), 3.28 (s, 3H, $CH_3$—O—), 3.42 to 3.46 (m, 2H, —$CH_2$—$N^+$—), 3.53 to 3.58 (m, 4H, —$CH_2$—O and —$CH_2$—$N^+$—), 3.87 to 3.91 (m, 2H, —$CH_2$—O—P=O), 4.16 to 4.18 (m, 4H, —$CH_2$—O—P=O and —$CH_2$—O—C=O), 5.62 (d, J=4, 1H, $CH_2$=C—) and 6.03 (d, J=4, 1H, $CH_2$=C—); $^{31}$P NMR (162 MHz, $D_2O$) δ ppm: -0.32; $^{13}$C NMR (100 MHz, $D_2O$) δ ppm: 17.27 ($CH_3$—C=$CH_2$—), 21.76 ($CH_2$—$CH_2$—$CH_2$—), 51.45 ($CH_3$—$N^+$—$CH_3$), 58.06 ($CH_3$—O—$CH_2$—), 59.13 (—$CH_2$—O—C=O), 61.85 (—$CH_2$—O—P=O), 62.78 (—$CH_2$—$N^+$—$CH_2$—), 64.67 (—$CH_2$—$N^+$—$CH_2$—), 64.73 (—$CH_2$—O—P=O), 71.46 ($CH_3$—O—$CH_2$—), 127.01 ($CH_2$=C—), 135.60 ($CH_2$=C—$CH_3$), 169.44 (O—C=O); FT-IR $v_{max}$/cm$^{-1}$: 2959 ($CH_2$ st.), 1717 (O—C=O st.), 1637 (C=C st.), 1456 (—$N^+(CH_3)_2$ def.), 1298 (P=O st.), 1239 (C—O—C st.), 1160 (C—N bend), 1059 (P—O—C st.), 950 (—$N(CH_3)_2$ st.), 842 ($CH_2$), 786 ($CH_2$); ESI LCMS for $C_{14}H_{29}NO_7P$ found m/z 354.1679 [M+H]$^+$ (calculated 354.1682) and $C_{14}H_{28}NO_7PNa$ found m/z 376.1497 [M+Na]$^+$ (calculated 376.1501).

Polymerization conditions for monomers synthesized in Examples 1-4 are as described in Examples 5-13 below.

Example 5

Polymerisation of the Novel Zwitterionic Materials

The zwitterion described in Example 2 (2-((2-(methacryloyloxy)ethyl) dimethylammonio)ethyl 2-methoxyethyl phosphate) was copolymerised with n-butyl methacrylate.

2-((2-(methacryloyloxy)ethyl)dimethylammonio)ethyl 2-methoxyethyl phosphate (10% mol) was blended in methanol with n-butyl methacrylate (90% mol) in a SCHOTT Duran pressure bottle. The concentration of monomers in solvent was 5.7M. The mixture was degassed by bubbling nitrogen through for 10 min. 2, 2'-Azobis-(2- methylbutyronitrile) (AMBN) (2.3×10$^{-2}$M) was quickly added, the bottle was sealed under N$_2$. The mixture was vigorously stirred at 400 rpm, at 125° C., for 60 min. The mixture became very viscous and was cooled down to room temperature. The viscous polymer was dissolved in twice the amount used of methanol and precipitated in hexane twice, followed by precipitation in water to yield 67% of a white polymer. The polymer was dissolved in isopropanol at a concentration of 48.2 g/L.

$^1$H NMR (400 MHz, MeOD) δ ppm: 0.91 (br. s, 6H, CH$_3$—C), 1.01 (br. s, 3H, CH$_3$—CH$_2$—), 1.48 (br. s, 2H, CH$_3$—CH$_2$—CH$_2$—), 1.67 (br. s, 2H, CH$_3$—CH$_2$—CH$_2$—), 1.88 to 2.23 (m, 4H, CH$_2$—C—), 3.35 (s, 6H, —N$^+$(CH$_3$)$_2$—), 3.39 (s, 3H, CH$_3$—O—), 3.60 (br. s, 2H, —CH$_2$—O—), 3.78 (br. s, 2H, —CH$_2$—N$^+$—), 3.87 (br. s, 2H, —CH$_2$—N$^+$—), 4.00 (br. s, 4H, —CH$_2$—O—C=O and —CH$_2$—O—P=O), 4.34 (br. s, 2H, —CH$_2$—O—P=O), 4.47 (br. s, 2H, —CH$_2$—O—C=O); $^{31}$P NMR (162 MHz, MeOD) δ ppm: −0.40; $^{13}$C NMR (176 MHz, MeOD) δ ppm: 13.08 (—CH$_2$—CH$_3$), 15.97 (—C—CH$_3$), 18.37 (—C—CH$_3$), 19.27 (CH$_3$—CH$_2$—), 30.12 (—CH$_2$—CH$_2$—), 44.64 (—C—CH$_3$), 44.95 (—C—CH$_3$), 51.75 (CH$_3$—N$^+$—CH$_3$), 54.58 (—CH$_2$—C—CH$_3$—), 57.86 (CH$_3$—O—), 58.80 (—CH$_2$—O—C=O and —CH$_2$—O—P=O), 64.60 to 64.70 (—CH$_2$—O—C=O, —CH$_2$—N$^+$(CH$_3$)$_2$ and —CH$_2$—O—P=O), 71.91 (—CH$_2$—O—CH$_3$), 176.73 (C=O), 177.62 (C=O); FT-IR $v_{max}$/cm$^{-1}$: 2959 (CH$_2$ st.), 1723 (O—C=O st.), 1466 (—N$^+$(CH$_3$)$_2$ def.), 1240 (O—P=O st. and C—O—C st.), 1144 (C—N bend), 1063 (P—O—C st.), 946 (—N(CH$_3$)$_2$ st.), 748 (CH$_2$); DSC: Tg=40° C. (±0.5° C.); Elemental analysis: found C: 61.16, H: 9.35, N: 0.86 and P: 1.48 (calculated C: 64.06, H: 9.57, N: 0.67 and P: 1.48).

Example 6

Polymerisation of the Novel Zwitterionic Materials 2-((2-(methacryloyloxy)ethyl)dimethylammonio)ethyl 2-methoxyethyl phosphate (20% mol) was blended in ethanol with n-butyl methacrylate (80% mol) in a SCHOTT Duran pressure bottle. The concentration of monomers in solvent was 1M. The mixture was degassed by bubbling nitrogen through for 10 min. Then the pressure bottle was sealed and heated up in an oil bath at 85° C. for 13 min. AMBN (4×10$^{-3}$M) was quickly added, the mixture degassed for 2 min and the bottle was sealed under N$_2$. The mixture was vigorously stirred at 400 rpm, at 120° C., for 3 h15 min. The mixture became very viscous and was cooled down to room temperature. The viscous polymer was dissolved ethanol and precipitated in hexane twice. In water, the polymer was becoming slightly soluble, thus, was dialysed overnight and freeze-dried for 2 days to yield 45% of a white powder. The polymer was dissolved in ethanol at a concentration of 30 g/L.

$^1$H NMR (400 MHz, MeOD) δ ppm: 0.90 (br. s, 6H, CH$_3$—C), 1.00 (br. s, 3H, CH$_3$—CH$_2$—), 1.47 (br. s, 2H, CH$_3$—CH$_2$—CH$_2$—), 1.66 (br. s, 2H, CH$_3$—CH$_2$—CH$_2$—), 1.88 to 2.15 (m, 4H, CH$_2$—C—), 3.36 (s, 6H, —N$^+$(CH$_3$)$_2$), 3.37 (s, 3H, CH$_3$—O—), 3.58 (br. s, 2H, —CH$_2$—O—), 3.80 (br. s, 2H, —CH$_2$—N$^+$—), 3.88 (br. s, 2H, —CH$_2$—N$^+$—), 3.99 (br. s, 4H, —CH$_2$—O—C=O and —CH$_2$—O—P=O), 4.34 (br. s, 2H, —CH$_2$—O—P=O), 4.47 (br. s, 2H, —CH$_2$—O—C=O); $^{31}$P NMR (162 MHz, MeOD) δ ppm: −0.37; $^{13}$C NMR (176 MHz, MeOD) δ ppm: 12.93 (—CH$_2$—CH$_3$), 15.93 (—C—CH$_3$), 17.05 (—C—CH$_3$), 19.22 (CH$_3$—CH$_2$—), 30.06 (—CH$_2$—CH$_2$—), 44.62 (—C—CH$_3$), 44.93 (—C—CH$_3$), 51.68 (CH$_3$—N$^+$—CH$_3$), 54.60 (—CH$_2$—C—CH$_3$—), 57.67 (CH$_3$—O—), 58.82 (—CH$_2$—O—C=O and —CH$_2$—O—P=O), 64.18 to 64.79 (—CH$_2$—O—C=O, —CH$_2$—N$^+$(CH$_3$)$_2$ and —CH$_2$—O—P=O), 71.84 (—CH$_2$—O—CH$_3$), 176.81 (C=O), 177.89 (C=O); FT-IR $v_{max}$/cm$^{-1}$: 2959 (CH$_2$ st.), 1724 (O—C=O st.), 1466 (—N$^+$(CH$_3$)$_2$ def.), 1238 (O—P=O st. and C—O—C st.), 1146 (C—N bend), 1060 (P—O—C st.), 947 (—N(CH$_3$)$_2$ st.), 748 (CH$_2$); DSC: Tg=69° C. (±0.5° C.).

Example 7

Polymerisation of the Novel Zwitterionic Materials 2-((2-(methacryloyloxy)ethyl)dimethylammonio)ethyl 2-methoxyethyl phosphate (30% mol) was blended in ethanol with n-butyl methacrylate (70% mol) in a SCHOTT Duran pressure bottle. The concentration of monomers in solvent was 1.7M. The mixture was degassed by bubbling nitrogen through for 10 min. Then the pressure bottle was sealed and heated up in an oil bath at 85° C. for 10 min. AMBN (6×10$^{-3}$M) was quickly added, the mixture degassed for 2 min and the bottle was sealed under N$_2$. The mixture was vigorously stirred at 400 rpm, at 120° C., for 2 h45 min. The mixture became very viscous and was cooled down to room temperature. The viscous polymer was dissolved in ethanol and precipitated in diethyl ether twice. In water, the polymer was becoming soluble, thus, was dialysed overnight and freeze-dried for 2 days to yield 53% of a white powder. The polymer was dissolved in ethanol at a concentration 30 g/L.

$^1$H NMR (400 MHz, MeOD) δ ppm: 0.81 (br. s, 6H, CH$_3$—C), 0.91 (br. s, 3H, CH$_3$—CH$_2$—), 1.37 (br. s, 2H, CH$_3$—CH$_2$—CH$_2$—), 1.56 (br. s, 2H, CH$_3$—CH$_2$—CH$_2$—), 1.68 to 2.10 (m, 4H, CH$_2$—C—), 3.25 (s, 6H, —N$^+$(CH$_3$)$_2$—), 3.29 (s, 3H, CH$_3$—O—), 3.50 (br. s, 2H, —CH$_2$—O—), 3.72 (br. s, 2H, —CH$_2$—N$^+$—), 3.80 (br. s, 2H, —CH$_2$—N$^+$—), 3.91 (br. s, 4H, —CH$_2$—O—C=O and —CH$_2$—O—P=O), 4.25 (br. s, 2H, —CH$_2$—O—P=O), 4.39 (br. s, 2H, —CH$_2$—O—C=O); $^{31}$P NMR (162 MHz, MeOD) δ ppm: −0.53; $^{13}$C NMR (176 MHz, MeOD) δ ppm: 12.96 (—CH$_2$—CH$_3$), 15.93 (—C—CH$_3$), 17.05 (—C—CH$_3$), 19.22 (CH$_3$—CH$_2$—), 30.05 (—CH$_2$—CH$_2$—), 44.63 (—C—CH$_3$), 44.93 (—C—CH$_3$), 51.69 (CH$_3$—N$^+$—CH$_3$), 54.70 (—CH$_2$—C—CH$_3$—), 57.82 (CH$_3$—O—), 58.83 (—CH$_2$—O—C=O and —CH$_2$—O—P=O), 64.57 and 64.82 (—CH$_2$—O—C=O, —CH$_2$—N$^+$(CH$_3$)$_2$ and —CH$_2$—O—P=O), 71.93 (—CH$_2$—O—CH$_3$), 177.00 (C=O), 177.51 (C=O); FT-IR $v_{max}$/cm$^{-1}$: 2959 (CH$_2$ st.), 1723 (O—C=O st.), 1467 (—N$^+$(CH$_3$)$_2$ def.), 1236 (O—P=O st. and C—O—C st.), 1147 (C—N bend), 1059 (P—O—C st.), 947 (—N(CH$_3$)$_2$ st.), 749 (CH$_2$); DSC: Tg=84° C. (±2.0° C.); Elemental analysis: found C: 51.87, H: 8.51, N: 1.99 and P: 4.32 (calculated C: 57.31, H: 8.88, N: 1.96 and P: 4.34).

Example 8

Polymerisation of the Novel Zwitterionic Materials 2-((3-(methacryloyloxy)propyl)dimethylammonio)ethyl 2-methoxyethyl phosphate from Example 4 (30% mol) was blended in ethanol with n-butyl methacrylate (70 mol %) in a SCHOTT Duran pressure bottle. The concentration of monomers in solvent was 1.7M. The mixture was degassed by bubbling N$_2$ through for 10 min. Then the pressure bottle was sealed and heated up in an oil bath at 80° C. for 10 min. AMBN ($6\times10^{-3}$ M) was quickly added, the mixture degassed for 2 min and the bottle was sealed under $N_2$. The mixture was vigorously stirred at 400 rpm, at 110° C. for 3 h. The mixture became very viscous and was cooled down to room temperature. The viscous polymer was dissolved in a minimum amount of ethanol and precipitated from hexane twice. Then, the polymer was dissolved in water, dialysed overnight and finally freeze-dried over 2 days to afford a white polymer in 41% yield.

$^1$H NMR (400 MHz, MeOD) δ ppm: 0.89 (br. s, 6H, $CH_3$—C—), 1.00 (br. s, 3H, $CH_3$—$CH_2$—), 1.40 (br. s, 2H, $CH_3$—$CH_2$—$CH_2$—), 1.66 (br. s, 2H, $CH_3$—$CH_2$—$CH_2$—), 1.86 to 2.09 (m, 4H, $CH_2$—C—), 2.24 (br. s, 2H, —$CH_2$—$CH_2$—$CH_2$—), 3.31 (s, 6H, —$N^+(CH_3)_2$—), 3.39 (s, 3H, $CH_3$—O—), 3.60 (br. s, 4H, —$CH_2$—O— and —$CH_2$—$N^+$—), 3.72 (br. s, 2H, —$CH_2$—$N^+$—), 4.00 (br. s, 2H, —$CH_2$—O—C=O), 4.12 (br. s, 2H, —$CH_2$—O—P=O), 4.32 (br. s, 4H, —$CH_2$—O—P=O and —$CH_2$—O—C=O); $^{31}$P NMR (162 MHz, MeOD) δ ppm: −0.30; $^{13}$C NMR (176 MHz, MeOD) δ ppm: 13.90 (—$CH_2$—$CH_3$), 16.80 (—C—$CH_3$), 18.37 (—C—$CH_3$), 18.37 ($CH_3$—$CH_2$—), 22.04 (—$N^+$—$CH_2$—$CH_2$—$CH_2$—O—), 30.06 (—$CH_2$—$CH_2$—), 44.64 (—C—$CH_3$), 44.93 (—C—$CH_3$), 51.03 ($CH_3$—$N^+$—$CH_3$), 54.50 (—$CH_2$—C—$CH_3$—), 57.70 ($CH_3$—O—), 58.73 and 58.82 (—$CH_2$—O—C=O and —$CH_2$—O—P=O), 61.94 (—$CH_2$—O—P=O), 64.26 (—$CH_2$—$N^+(CH_3)_2$), 64.54 and 64.57 ($CH_2$—O—C=O and —$CH_2$—$N^+(CH_3)_2$), 71.94 (—$CH_2$—O—$CH_3$), 176.91 (C=O), 177.67 (C=O); FT-IR $v_{max}$/cm$^{-1}$: 2959 ($CH_2$ st.), 1723 (O—C=O st.), 1467 (—$N^+(CH_3)_2$ def.), 1236 (O—P=O st. and C—O—C st.), 1154 (C—N bend), 1058 (P—O—C st.), 948 (—$N(CH_3)_2$ st.), 748 ($CH_2$); DSC: Tg=79° C. (±1.0° C.).

Example 9

Polymerisation of the Novel Zwitterionic Materials 2-((2-(methacryloyloxy)ethyl)dimethylammonio)ethyl 2-methoxyethyl phosphate (20% mol) was blended in methanol with hexyl methacrylate (30% mol) and methoxyethyl methacrylate (50%) in a SCHOTT Duran pressure bottle. The concentration of monomers in solvent was 4.9M. The mixture was degassed by bubbling nitrogen through for 10 min. Then the pressure bottle was sealed and heated up in an oil bath at 85° C. for 10 min. AMBN ($2\times10^{-2}$M) was quickly added, the mixture degassed for 2 min and the bottle was sealed under $N_2$. The mixture was vigorously stirred at 400 rpm, at 120° C., for 3 h. The mixture became very viscous and was cooled down to room temperature. The viscous polymer was dissolved in methanol and precipitated in diethyl ether twice. The polymer was slightly soluble in water and was dialysed overnight. The dry polymer was obtained in 31% yield after freeze-drying over 3 days. The white powder was dissolved in ethanol at a concentration of 30 g/L.

$^1$H NMR (400 MHz, MeOD) δ ppm: 0.85 to 1.18 (m, 12H, $CH_3$—C— and $CH_3$—$CH_2$—), 1.39 (br. s, 6H, —$CH_2$—$CH_2$—$CH_2$— and $CH_3$—$CH_2$—$CH_2$—), 1.68 (br. s, 2H, —O—$CH_2$—$CH_2$—), 1.88 to 2.16 (m, 6H, $CH_2$—C—), 3.31 (s, 6H, —$N^+(CH_3)_2$—), 3.37 (s, 6H, $CH_3$—O—), 3.63 (br. s, 4H, —$CH_2$—O—), 3.78 (br. s, 2H, —$CH_2$—$N^+$—), 3.87 (br. s, 2H, —$CH_2$—$N^+$—), 3.99 (br. s, 4H, —$CH_2$—O—C=O and —$CH_2$—O—P=O), 4.13 (br. s, 2H, —$CH_2$—O—C=O), 4.34 (br. s, 2H, —$CH_2$—O—P=O), 4.47 (br. s, 2H, —$CH_2$—O—C=O); $^{31}$P NMR (162 MHz, MeOD) δ ppm: −0.49; $^{13}$C NMR (176 MHz, MeOD) δ ppm: 14.02 ($CH_3$—$CH_2$—), 16.00 to 18.02 (—C—$CH_3$), 22.40 (—$CH_2$—$CH_2$—$CH_2$—), 25.73 (—$CH_2$—$CH_2$—$CH_2$—), 27.93 (—O—$CH_2$—$CH_2$—), 31.34 ($CH_3$—$CH_2$—), 44.64 (—C—$CH_3$), 44.95 (—C—$CH_3$), 51.57 ($CH_3$—$N^+$—$CH_3$), 54.33 (—$CH_2$—C—$CH_3$), 57.74 ($CH_3$—O—), 57.87 ($CH_3$—O—), 58.78 (—$CH_2$—O—C=O and —$CH_2$—O—P=O), 63.73 to 64.97 (—$CH_2$—O—C=O, —$CH_2$—$N^+(CH_3)_2$ and —$CH_2$—O—P=O), 69.69 (—$CH_2$—O—$CH_3$), 71.82 (—$CH_2$—O—$CH_3$), 176.05 (C=O), 177.69 (C=O); FT-IR $v_{max}$/cm$^{-1}$: 2932 ($CH_2$ st.), 1724 (O—C=O st.), 1455 (—$N^+(CH_3)_2$ def.), 1239 (O—P=O st. and C—O—C st.), 1151 (C—N bend), 1061 (P—O—C st.), 959 (—$N(CH_3)_2$ st.), 748 ($CH_2$); DSC: Tg=54° C. (±2.0° C.).

Example 10

Polymerisation of the Novel Zwitterionic Materials 2-((2-(methacryloyloxy)ethyl)dimethylammonio)ethyl 2-methoxyethyl phosphate (30% mol) was blended in ethanol with hexyl methacrylate (30% mol) and methoxyethyl methacrylate (40%) in a SCHOTT Duran pressure bottle. The concentration of monomers in solvent was 1.05M. The mixture was degassed by bubbling nitrogen through for 13 min. Then the pressure bottle was sealed and heated up in an oil bath at 85° C. for 10 min. AMBN ($3.9\times10^{-3}$M) was quickly added, the mixture degassed for 2 min and the bottle was sealed under $N_2$. The mixture was vigorously stirred at 400 rpm, at 120° C., for 3 h30. The mixture became very viscous and was cooled down to room temperature. The viscous polymer was dissolved in ethanol and precipitated in hexane twice. The polymer was slightly soluble in water and was dialysed overnight. The dry polymer was obtained in 71% yield after freeze-drying over 3 days. The white powder was dissolved in ethanol at a concentration of 30 g/L.

$^1$H NMR (400 MHz, MeOD) δ ppm: 0.88 to 1.20 (m, 12H, $CH_3$—C— and $CH_3$—$CH_2$—), 1.39 (br. s, 6H, —$CH_2$—$CH_2$—$CH_2$— and $CH_3$—$CH_2$—$CH_2$—), 1.61 (br. s, 2H, —O—$CH_2$—$CH_2$—), 1.80 to 2.16 (m, 6H, $CH_2$—C—), 3.36 (s, 6H, —$N^+(CH_3)_2$—), 3.39 (s, 6H, $CH_3$—O—), 3.61 (br. s, 4H, —$CH_2$—O—), 3.81 (br. s, 2H, —$CH_2$—$N^+$—), 3.91 (br. s, 2H, —$CH_2$—$N^+$—), 4.01 (br. s, 4H, —$CH_2$—O—C=O and —$CH_2$—O—P=O), 4.14 (br. s, 2H, —$CH_2$—O—C=O), 4.36 (br. s, 2H, —$CH_2$—O—P=O), 4.48 (br. s, 2H, —$CH_2$—O—C=O); $^{31}$P NMR (162 MHz, MeOD) δ ppm: −0.42; $^{13}$C NMR (176 MHz, MeOD) δ ppm: 14.00 ($CH_3$—$CH_2$—), 16.12 to 18.20 (—C—$CH_3$), 22.36 (—$CH_2$—$CH_2$—$CH_2$—), 25.70 (—$CH_2$—$CH_2$—$CH_2$—), 27.88 (—O—$CH_2$—$CH_2$—), 31.29 ($CH_3$—$CH_2$—), 44.62 (—C—$CH_3$), 44.94 (—C—$CH_3$), 51.70 ($CH_3$—$N^+$—$CH_3$), 53.24 to 56.07 (—$CH_2$—C—$CH_3$), 57.64 ($CH_3$—O—), 57.70 ($CH_3$—O—), 58.53 and 58.82 (—$CH_2$—O—C=O and —$CH_2$—O—P=O), 63.26 to 64.94 (—$CH_2$—O—C=O, —$CH_2$—$N^+(CH_3)_2$ and —$CH_2$—O—P=O), 69.66 (—$CH_2$—O—$CH_3$), 71.93 (—$CH_2$—O—$CH_3$), 176.82 (C=O), 177.67 (C=O); FT-IR $v_{max}$/cm$^{-1}$: 2932 ($CH_2$ st.), 1725 (O—C=O st.), 1456 (—$N^+(CH_3)_2$ def.), 1236 (O—P=O st. and C—O—C st.), 1151 (C—N bend), 1059 (P—O—C st.), 952 (—$N(CH_3)_2$ st.), 748 ($CH_2$); DSC: Tg=66° C. (±0.5° C.).

Example 11

Polymerisation of the Novel Zwitterionic Materials 2-((2-(methacryloyloxy)ethyl)dimethylammonio)ethyl 2-methoxyethyl phosphate 11%) was blended in methanol with hexyl methacrylate (31% mol) and hydroxypropyl methacrylate (58%) in a SCHOTT Duran pressure bottle. The concentration of monomers in solvent was 5.4M. The mixture was degassed by bubbling nitrogen through for 15 min. Then the pressure bottle was sealed and heated up in an oil bath at 85° C. for 10 min. AMBN ($2.6 \times 10^{-2}$M) was quickly added, the mixture degassed for 2 min and the bottle was sealed under $N_2$. The mixture was vigorously stirred at 400 rpm, at 120° C., for 1 h20. The mixture became very viscous and was cooled down to room temperature. The viscous polymer was dissolved in methanol and precipitated in cold water and washed 3 times. The polymer eventually dissolved in water and was dialysed overnight. The dry polymer was obtained in 36% yield after freeze-drying over 3 days. The white powder was dissolved in ethanol at a concentration of 30 g/L.

$^1$H NMR (400 MHz, MeOD) δ ppm: 0.96 to 1.18 (br. s, 12H, $CH_3$— and $CH_3$—$CH_2$), 1.23 (br. s, 6H, —CH—$CH_3$), 1.38 (br. s, 6H, —$CH_2$—$CH_2$—$CH_2$— and $CH_3$—$CH_2$—$CH_2$—), 1.67 (br. s, 2H, —O—$CH_2$—$CH_2$—), 1.80 to 2.16 (m, 6H, —$CH_2$—C—), 3.35 (s, 6H, —$N^+(CH_3)_2$—), 3.37 (s, 3H, $CH_3$—O—), 3.61 (br. s, 4H, —$CH_2$—O— and —CH—$CH_2$—), 3.85 (br. s, 7H, —$CH_2$—$N^+$—, O=C—O—$CH_2$— and —O—$CH_2$—CH—), 3.99 (br. s, 4H, —$CH_2$—O—C=O and —$CH_2$—O—P=O), 4.34 (br. s, 2H, —$CH_2$—O—P=O), 4.47 (br. s, 2H, —$CH_2$—O—C=O), 4.76 (br. s, 1H, $CH_3$—CH—$CH_2$—); $^{31}$P NMR (162 MHz, MeOD) δ ppm: −0.37; $^{13}$C NMR (176 MHz, MeOD) δ ppm: 14.80 ($CH_3$—$CH_2$—), 15.94 (—C—$CH_3$), 16.05 (—C—$CH_3$), 16.25 (—C—$CH_3$), 18.87 (—CH—$CH_3$), 22.37 (—$CH_2$—$CH_2$—$CH_2$—), 25.71 (—$CH_2$—$CH_2$—$CH_2$—), 27.91 (—O—$CH_2$—$CH_2$—), 31.31 ($CH_3$—$CH_2$—), 44.63 (—C—$CH_3$), 44.97 (—C—$CH_3$), 51.79 ($CH_3$—$N^+$—$CH_3$), 54.25 (—$CH_2$—C—$CH_3$), 57.73 ($CH_3$—O—), 58.81 (—$CH_2$—O—C=O and —$CH_2$—O—P=O), 63.24 to 65.03 (—$CH_2$—O—C=O, —CH—$CH_3$, —CH—$CH_2$—, —$CH_2$—$N^+(CH_3)_2$ and —$CH_2$—O—P=O), 69.72 (—$CH_2$—O—C=O), 71.94 (—$CH_2$—O—$CH_3$), 176.86 (C=O), 177.77 (C=O); FT-IR $ν_{max}$/cm$^{-1}$: 3379 (OH st.), 2932 ($CH_2$ st.), 1722 (O—C=O st.), 1453 (—$N^+(CH_3)_2$ def.), 1239 (O—P=O st. and C—O—C st.), 1148 (C—N bend), 1058 (P—O—C st.), 962 (—N$(CH_3)_2$ st.), 748 ($CH_2$); DSC: Tg=95° C. (±0.5° C.); Elemental analysis: found C: 55.87, H: 8.88, N: 0.91 and P: 2.13 (calculated C: 59.83, H: 8.98, N: 0.79 and P: 1.74).

Example 12

Polymerisation of the Novel Zwitterionic Materials 2-((2-(methacryloyloxy)ethyl)dimethylammonio)ethyl 2-methoxyethyl phosphate (20% mol) was blended in ethanol with hexyl methacrylate (30% mol) and hydroxypropyl methacrylate (50%) in a SCHOTT Duran pressure bottle. The concentration of monomers in solvent was 1M. The mixture was degassed by bubbling nitrogen through for 13 min. Then the pressure bottle was sealed and heated up in an oil bath at 85° C. for 10 min. AMBN ($4 \times 10^{-3}$M) was quickly added, the mixture degassed for 2 min and the bottle was sealed under $N_2$. The mixture was vigorously stirred at 400 rpm, at 120° C., for 2 h45. The mixture became very viscous and was cooled down to room temperature. The viscous polymer was dissolved in ethanol and precipitated in hexane and washed twice. The polymer was dissolved in water and dialysed overnight. The dry polymer was obtained in 62% yield after freeze-drying over 3 days. The white powder was dissolved in ethanol at a concentration of 30 g/L.

$^1$H NMR (400 MHz, MeOD) δ ppm: 0.89 to 1.19 (br. s, 12H, $CH_3$— and $CH_3$—$CH_2$—), 1.24 (br. s, 6H, —CH—$CH_3$), 1.39 (br. s, 6H, —$CH_2$—$CH_2$—$CH_2$— and $CH_3$—$CH_2$—$CH_2$—), 1.68 (br. s, 2H, —O—$CH_2$—$CH_2$—), 1.80 to 2.16 (m, 6H, —$CH_2$—C—), 3.36 (s, 6H, —$N^+(CH_3)_2$—), 3.40 (s, 3H, $CH_3$—O—), 3.61 (br. s, 4H, —$CH_2$—O— and —CH—$CH_2$—), 3.86 (br. s, 5H, —$CH_2$—$N^+$—, $CH_3$—CH—OH), 4.01 (br. s, 6H, —$CH_2$—O—P=O and —$CH_2$—O—C=O), 4.36 (br. s, 2H, —$CH_2$—O—P=O), 4.49 (br. s, 2H, —$CH_2$—O—C=O), 4.79 (br. s, 1H, $CH_3$—CH—$CH_2$—); $^{31}$P NMR (162 MHz, MeOD) δ ppm: −0.40; $^{13}$C NMR (176 MHz, MeOD) δ ppm: 14.80 ($CH_3$—$CH_2$—), 15.92 (—C—$CH_3$), 16.03 (—C—$CH_3$), 18.88 (—CH—$CH_3$), 22.35 (—$CH_2$—$CH_2$—$CH_2$—), 25.69 (—$CH_2$—$CH_2$—$CH_2$—), 27.89 (—O—$CH_2$—$CH_2$—), 31.29 ($CH_3$—$CH_2$—), 44.63 (—C—$CH_3$), 44.94 (—C—$CH_3$), 51.75 ($CH_3$—$N^+$—$CH_3$), 54.17 (—$CH_2$—C—$CH_3$), 57.67 ($CH_3$—O—), 58.45 and 58.82 (—$CH_2$—O—C=O and —$CH_2$—O—P=O), 63.24, 64.58, 64.80 and 65.02 (—$CH_2$—O—C=O, —CH—$CH_3$, —CH—$CH_2$—, —$CH_2$—$N^+(CH_3)_2$ and —$CH_2$—O—P=O), 69.72 (—CH—$CH_2$—), 71.94 (—$CH_2$—O—$CH_3$), 176.86 (C=O), 177.77 (C=O); FT-IR $ν_{max}$/cm$^{-1}$: 3357 (OH st.), 2932 ($CH_2$ st.), 1722 (O—C=O st.), 1455 (—$N^+(CH_3)_2$ def.), 1234 (O—P=O st. and C—O—C st.), 1148 (C—N bend), 1057 (P—O—C st.), 951 (—N$(CH_3)_2$ st.), 749 ($CH_2$); DSC: Tg=99° C. (±2.5° C.).

Example 13

Contact Lenses Formation

The zwitterion synthesised in Example 4 (2-((3-(methacryloyloxy)propyl)dimethylammonio)ethyl 2-methoxyethyl phosphate) was used to prepare contact lenses.

Hydroxyethyl methacrylate (Cognis) was blended with ethylene glycol dimethacrylate (Aldrich) (0.2% mol). The mixture was vortexed and degas sed by 3 cylces of freeze-pump-thaw. Perkadox16 (AkzoNobel) (0.1% mol) was added, dissolved and the mixture was degassed by one cycle of freeze-pump-thaw.

The previous mixture containing hydroxyethyl methacrylate, ethylene glycol dimethacrylate and Perkadox16 was blended (80% w/w) with (2-((3-(methacryloyloxy)propyl)dimethylammonio)ethyl 2-methoxyethyl phosphate) (example 4, 20% w/w) to form a polymerizable contact lens formulation. The polymerizable contact lens formulation was degassed by one cycle of freeze-pump-thaw. The degassed polymerizable contact lens formulation (60 μL) was placed in a female polypropylene mold (concave optical quality surface) and sealed with the male polypropylene mold (convex optical quality surface).

The contact lens mold containing the polymerizable contact lens formulation was placed in an oven at 80° C. for a period of 2 hours, allowing the polymerizable contact lens formulation to cure completely. After the curing process, the mold was taken out of the vacuum oven and left to cool down to room temperature (20° C.). The contact lens mold was mechanically open to separate the male and female mold members. The polymerised contact lens was removed carefully from the mold and immediately immersed in a solution of phosphate buffered saline (PBS).

Elemental analysis: found C: 50.93, H: 7.83, N: 0.70 and P: 1.35 (calculated C: 55.81, H: 7.79, N: 0.79 and P: 1.75)

Example 14

Water Content in the Contact Lenses

After one hour immersion in the PBS solution, the lens produced from Example 13 was tapped on a tissue paper to remove excess water and the weight of the hydrated lens was recorded. Then, the hydrated lens was placed on a Teflon sheet and dried in an oven at 60° C. to constant weight (~2 hours). The weight of the dried lens was recorded. The water content percent was calculated using the following equation and referred to as EWC (equilibrium water content):

$$EWC\ \% = \frac{weight_{wet} - weight_{dry}}{weight_{wet}} \times 100$$

The EWC of the lens was 59%, higher in comparison to a lens containing a formulation of 2-hydroxyethyl methacrylate, which displayed a water content of 38%. The dried lens was successfully rehydrated in PBS and retrieved its complete transparency.

Example 15

Lysozyme and Albumin Adsorption on the Surface of the Lenses

The lens prepared in Example 13 was incubated in either 4 mL of an albumin solution in PBS at 2 mg/mL or 4 mL of a lysozyme solution in PBS at 2 mg/mL for 2 hours at 37° C. The lens was rinsed subsequently by 3 washes in fresh PBS and was then sonicated in sodium dodecyl sulfate at 1% (w/w) in PBS for 30 min. 1 mL of the sonicated solution was mixed in a borosilicate tube with 1 mL of a microBCA reagent (Pierce, Thermo Scientific) and incubated at 60° C. for 1 hour. Once the tubes were cooled down, their absorbance was read at 562 nm. The amount of protein adsorbed on the lens was calculated from standard curves from each specific protein that were fitted with a polynomial curve. The amount of protein adsorbed onto the lens prepared in Example 13 is given below:

Bovine serum albumin: 0.38 (±0.18) µg/cm$^2$
Chicken egg-white lysozyme: 0.61 (±0.06) µg/cm$^2$ The lenses were then incubated for a period of 15 consecutive days in a lysozyme solution at 2 mg/mL. The solution were changed daily and after 15 days the lens was rinsed by 3 washes in fresh PBS and was then sonicated in sodium dodecyl sulfate at 1% (w/w) in PBS for 30 min. 1 mL of the sonicated solution was mixed in a borosilicate tube with 1 mL of a microBCA reagent (Pierce, Thermo Scientific) and incubated at 60° C. for 1 hour. Once the tubes were cooled down, their absorbance was read at 562 nm. The amount of lysozyme adsorbed on the lens after 15 days was 1.95 (±0.05) µg/cm$^2$.

Example 16

Platelet Adhesion on a Coated Cover Slip (Polystyrene)

Human blood was collected from a healthy volunteer donor. 14 mL of a CPD (citrate phosphate dextrose) solution in PBS (phosphate buffered saline) was added to 100 mL of fresh blood. A 100 mL solution of CPD contains trisodium citrate (tribasic) (2.63 g), citric acid (0.377 g), sodium dihydrogen phosphate (0.222 g) dextrose/glucose (2.55 g) and water up to 100 mL. CPD is used as an anticoagulant, particularly used with platelets as the dextrose/glucose feed the platelets. The blood containing CPD was centrifuged at 800G for 5 minutes to separate PRP (platelet rich plasma). After separation, the rest of the blood was further centrifuged at 3000G for 10 minutes to obtain PPP (platelet poor plasma). Then, PRP was diluted with PPP to adjust the number of platelets to 1×10$^5$ platelets/µL to form an adjusted PRP. Each of the polymer described in examples 5-12, in an alcoholic solution was dip-coated on the surface of a polystyrene cover slip (Agar 22×22 mm) and dried in an oven at 50° C. for 1 hour. Specifically, the coverslip was dip-coated in a solution containing the copolymer at 3% in ethanol. The coverslip was introduced in the solution, left for 10 seconds and slowly removed from the solution. The coverslips were then dried in an oven at 60° C. for one hour.

The adjusted PRP solution (200 µL, 1×10$^5$ platelets/µL) was dripped onto the coated cover slip and left to stand at room temperature for 30 min. The sample was rinsed twice using a solution of PBS and the platelets were fixed on the coated disc using 2.5% (vol %) PBS solution of glutaraldehyde over 1 hour. The coated cover slip was observed under an inverted microscope (Motic AE31×400). Results are presented in Table 1 below. The coated cover slips appear to have improved haemocompatible properties compared to uncoated cover slip represented by significantly reduced platelets and aggregates found on the cover slips.

TABLE 1

| Polymer Coating | Coating Composition (mol %) | platelets/mm$^2$ | Number of aggregates | % Reduction |
|---|---|---|---|---|
| Uncoated | Polystyrene disc | 12184 | 20 | 0 |
| Example 5 | n-butyl methacrylate 90% novel ampholyte 10% | 2441 | 4 | 80 |
| Example 6 | n-butyl methacrylate 80% novel ampholyte 20% | 1915 | 1 | 84 |
| Example 7 | n-butyl methacrylate 70% novel ampholyte 30% | 968 | 0 | 92 |
| Example 8 | n-butyl methacrylate 70% novel ampholyte 30% | 1832 | 1 | 85 |
| Example 9 | hexyl methacrylate 30% methoxylethyl methacrylate 50% novel ampholyte 20% | 1471 | 2 | 88 |
| Example 10 | hexyl methacrylate 30% methoxylethyl methacrylate 40% novel ampholyte 30% | N/A | N/A | N/A |

TABLE 1-continued

| Polymer Coating | Coating Composition (mol %) | platelets/mm² | Number of aggregates | % Reduction |
|---|---|---|---|---|
| Example 11 | hexyl methacrylate 31% hydroxypropyl methacrylate 58% novel ampholyte 11% | 1540 | 0 | 87 |
| Example 12 | hexyl methacrylate 30% hydroxypropyl methacrylate 50% novel ampholyte 20% | 958 | 1 | 92 |

Example 17

Protein Adsorption on Coated Wells

Wells of 24-well plates were coated with polymeric solution of examples 5, 6, 7, 8, 9 and 11 at 5 mg/mL. Solutions of bovine plasma fibrinogen at 0.3 mg/mL in PBS and bovine serum albumin at 4.5 mg/mL were prepared, protein concentrations corresponding to 10% of the plasma protein level. The coated wells were incubated for 2 hours in a specified protein solution at 37° C. The wells containing the solution were rinsed with fresh PBS twice and the wells were sonicated with a sodium dodecyl sulfate solution at 1% (w/w) in PBS for 30 minutes. 1 mL of the sonicated solution was mixed in a borosilicate tube with 1 mL of a microBCA reagent (Pierce, Thermo Scientific) and incubated at 60° C. for 1 hour. Once the tubes were cooled down, their absorbance was read at 562 nm. The amount of protein adsorbed on the wells was calculated from standard curves from each specific protein that were fitted with a polynomial curve. The amount of protein adsorbed onto the wells prepared in Examples 5, 6, 7, 8, 9 and 11 and controls is given below:

TABLE 2A

| Well Coating | Composition | bovine plasma fibrinogen µg/cm² ± Std. Dev. | % Reduction |
|---|---|---|---|
| Uncoated | Uncoated polystyrene well | 1.92 (±0.19) | — |
| Poly(BMA) | Poly(butyl methacrylate) | 2.80 (±0.29) | — |
| Example 5 | n-butyl methacrylate 90% novel ampholyte 10% | 0.58 (±0.02) | 79% |
| Example 6 | n-butyl methacrylate 80% novel ampholyte 20% | 0.46 (±0.14) | 84% |
| Example 7 | n-butyl methacrylate 70% novel ampholyte 30% | 0.21 (±0.14) | 93% |
| Example 8 | n-butyl methacrylate 70% novel ampholyte 30% | 0.38 (±0.14) | 86% |
| Example 9 | hexyl methacrylate 30% methoxylethyl methacrylate 50% novel ampholyte 20% | 0.79 (±0.13) | 72% |
| Example 11 | hexyl methacrylate 31% hydroxypropyl methacrylate 58% novel ampholyte 11% | 0.54 (±0.18) | 81% |

TABLE 2B

| Well Coating | Composition | bovine serum albumin µg/cm² ± Std. Dev. | % Reduction |
|---|---|---|---|
| Uncoated | Uncoated polystyrene well | 1.38 (±0.48) | — |
| Poly(BMA) | Poly(butyl methacrylate) | 1.54 (±0.37) | — |
| Example 5 | n-butyl methacrylate 90% novel ampholyte 10% | 0.15 (±0.15) | 90% |
| Example 6 | n-butyl methacrylate 80% novel ampholyte 20% | 0.10 (±0.09) | 94% |
| Example 7 | n-butyl methacrylate 70% novel ampholyte 30% | 0.10 (±0.09) | 94% |
| Example 8 | n-butyl methacrylate 70% novel ampholyte 30% | 0.16 (±0.01) | 90% |
| Example 9 | hexyl methacrylate 30% methoxylethyl methacrylate 50% novel ampholyte 20% | 0.18 (±0.13) | 88% |
| Example 11 | hexyl methacrylate 31% hydroxypropyl methacrylate 58% novel ampholyte 11% | 0.07 (±0.06) | 96% |

Example 18

Lens Epithelial Cells Growth on Coatings Containing the Novel Ampholyte

Lens epithelial cells from rabbit were seeded at a concentration of $1 \times 10^4$ cells/cm² in a minimum essential media eagle into 24-well plates coated with various polymeric solution from examples 5, 6, 7, 9 and 11 and from a solution of poly(butyl methacrylate). The solution were adjusted at 0.5% (w/v) in methanol or isopropanol and coated onto the surface of the 24-well plate to provide a homogeneous coating. The wells containing the cells were then incubated at 37° C. for 1, 4 and 7 days and the growth of cells at these time points was evaluated.

At the different time points, the wells were observed under inverted microscopy and then treated for fluorescence evaluation with phalloidin and DAPI (4',6-diamidino-2-phenylindole). The cells were counted and the results reported in Table 3.

TABLE 3

| 24-Wells coated | Composition | Cell count at Day 1 ± Std. Dev | Cell count at Day 4 ± Std. Dev | Cell count at Day 7 ± Std. Dev |
|---|---|---|---|---|
| Uncoated | | 110.83 ± 8.14 | 110.25 ± 74.08 | 1369.42 ± 22.42 |
| Poly(butyl methacrylate | Poly(butyl methacrylate) | 4.50 ± 1.75 | 495.58 ± 120.32 | 766.00 ± 206.35 |
| Example 5 | n-butyl methacrylate 90% novel ampholyte 10% | 0.92 ± 1.42 | 0 | 0 |
| Example 6 | n-butyl methacrylate 80% novel ampholyte 20% | 0 | 0 | 0 |
| Example 7 | n-butyl methacrylate 70% novel ampholyte 30% | 88.17 ± 18.51 | 495.50 ± 275.37 | 816.08 ± 378.30 |
| Example 9 | hexyl methacrylate 30% methoxylethyl methacrylate 50% novel ampholyte 20% | 2.58 ± 2.50 | 4.00 ± 3.54 | 21.67 ± 31.21 |
| Example 11 | hexyl methacrylate 31% hydroxypropyl methacrylate 58% novel ampholyte 11% | 0 | 0 | 0 |

The embodiments set forth herein are intended to be illustrative and not limiting. Additional embodiments are within the claims. All patent applications, patents, references and publications set forth herein are hereby incorporated by reference herein for all purposes: in case of conflict with the specification, the specification is controlling.

REFERENCES

All references listed below are hereby incorporated herein by reference.

(1) Williams, D. F. *The Williams Dictionary of Biomaterials*; Liverpool University Press, 1999.

(2) Williams, D. F. In *European Society for Biomaterials*; Elsevier: Amsterdam, 1987.

(3) Williams, D. F. *Biomaterials*, 2009, 30, 5897.

(4) Iwasaki, Y.; Ishihara, K. *Anal. Bioanal. Chem.*, 2005, 381, 534.

(5) Hirota, K.; Murakami, K.; Nemoto, K.; Miyake, Y. *FEMS Microbiol. Lett.*, 2005, 248, 37.

(6) Hukins, D. W. L.; Leahy, J. C.; Mathias, K. *J. J. Mater. Chem.*, 1999, 9, 629.

(7) Lucas, H. J.; Mitchell, F. W.; Scully, C. N. *J. Am. Chem. Soc.*, 1950, 72, 5491.

(8) Edmundson, R. S. *Chem. Ind. (London)*, 1962, 42, 1828.

(9) Nakaya, T.; Li, Y. *J. Prog. Polym. Sci.*, 1999, 24, 143.

(10) Kiritoshi, Y., Ishihara, K. *Polymer*, 2004, 45, 7499.

(11) Chapman, D., Royal Free Hospiotal School of Medicine, Patent EP0032622B1

(12) Tsubone, K., Uchida, N. *JAOCS*, 1990, 76, 394.

(13) Nakaya, T., Yasuzawa, M., Imoto, M., *Macromol Reports*, 1994, A31 (supl 1&2), 207.

(14) Furukawa, A., Nakaya, T., Imoto, M., *J. Macromol. Sci. Chem.*, 1988, A25, 3, 337.

(15) Nakaya, T., Yasuzawa, M., Imoto, M., *Macromol.*, 1989, 22, 3180.

(16) Nakaya, T., Yasuzawa, M., Yamada, M., *Chem. Express*, 1992, 7, 861.

(17) Nakaya, T., Yasuzawa, M., Imoto, M., *Makromol. Chem., Rapid, Commun.*, 1985, 6, 721.

(18) Phosphoric acid esters, their preparation and their use for the preparation of biocompatible surfaces, EP 01557469, 1985, Chapman D. Durrani, A. A., Biocompatibles ltd.

(19) Polymerisable phospholipids and polymers thereof, methods for their preparation, methods for their use in coating substrates and forming liposomes and the resulting coated substrates and liposome compositions, EP0032622, 1985, Chapman, D., Royal Free Hospital School of Medicine.

(20) Compound having phospholipid analogous structure, polymer and production thereof JP 63222183 (A), 1988, Nakaya T. Oki Electric.

(21) Compound having lipid like structure and polymer and their preparation, JP 59199696 (A), 1984, JP 3031718 (B), 1991, JP 1689625 (C), 1992, Nakaya T. Oki Electric.

(22) Compound similar to that of phospholipids and its polymer and production thereof, JP 59164331 (A), 1984, JP 6305144 (B), 1988, JP 1501722 (C), 1989, Nakaya T. Oki Electric.

(23) Compound and polymer having structure similar to natural phospholipid and production thereof, JP 2238007 (A), 1990, JP 6076459 (B), 1994, JP 1941652 (C), 1995, Nakaya T. Oki Electric.

(24) Polymer from compound having phospholipid-like structure, JP 63086704 (A), 1988, JP 3016364 (B), 1991, JP 1656626 (C), 1992, Nakaya T. Oki Electric.

(25) (2-oxo-1,3,2-dioxaphosphoryl)glycoxy-2-oxo-1,3,2-dioxaphosphorane and production thereof, JP 62270591 (A), 1987, JP 2009034 (B), 1990, JP 1586838 (C), 1990, Nakaya T. Oki Electric.

(26) Compound having phospholipid analogous structure, polymer and production thereof, JP 6179408 (A), 1985, JP 63222185 (B), 1988, Nakaya T. Oki Electric.

(27) Preparation of monomer analogous to phospholipid, JP 58154591 (A), JP 2049316 (B), JP 1624024 (C), Compound having phospholipid analogous structure, polymer and production thereof, JP 63222185 (B), 1988, Nakaya T. Oki Electric.

(28) Antithrombotic surface treating agent and medical apparatus, U.S. Pat. No. 6,590,054 B2, 2003, Tanaka M, Ochiai S., Tokunaga N., Irie Y, Terumo Kabushiki Kaisha.

The invention claimed is:

1. A compound comprising a polymer that comprises a polymer backbone and an ampholyte compound pendant group, with said compound being represented by a general formula:

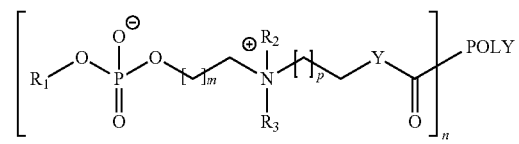

wherein POLY represents the polymer backbone, wherein Y represents an oxygen in an ester moiety or a secondary amine in an amide moiety, wherein m and p independently range from 0 to 6, with an m of 1 to 6 denoting a hydrocarbon chain referred to as the m-hydrocarbon chain and a p in a range from 1 to 6 denoting a hydrocarbon chain referred to as the p-hydrocarbon chain, wherein n is at least one and indicates a number of pendant groups that are independently selected and independently attached to the polymer backbone, and wherein $R_1$ is hydrophilic and chosen from the group consisting of (a) a substituted alkyl group, (b) a substituted cycloalkyl group, (c) a substituted cycloalkenyl group, (d) a substituted or unsubstituted heterocycle group, and (e) a substituted alkenyl group, wherein the $R_1$ group terminates with a methoxy group;

wherein $R_2$ and $R_3$, are independently chosen from the group consisting of
(a) a substituted or unsubstituted alkyl group, (b) a substituted or unsubstituted aryl group,(c) a substituted or unsubstituted cycloalkyl group, (d) a substituted or unsubstituted cycloalkenyl group, (e) a substituted or unsubstituted heterocycle group, and (f) a substituted or unsubstituted alkenyl group; and wherein the m-hydrocarbon chain and/or the p-hydrocarbon chain are substituted or unsubstituted hydrocarbon chains, wherein if the hydrocarbon chain is substituted substitution is an attachment to the hydrocarbon chain or is a heteroatom within the hydrocarbon chain.

2. The compound of claim 1 wherein the polymer backbone is chosen from the group consisting of polycarbonate, polyacrylate, polymethacrylate, polyester, polysiloxane, polyacrylamide, and polyurethane.

3. The compound of claim 1 wherein the polymer further comprises one or more further pendant groups chosen from the group consisting of methyl group, ethyl group, propyl group, butyl group, hydroxyethyl group, hydroxypropyl group, hexyl group, methoxyethyl group, methacrylic acid group, epoxy group, poly(hexanide) group, alkyl derivatized poly(hexanide) group, poly(ethylene glycol) group, heparin group, and benzoylphenyl group.

4. The compound of claim 1 wherein the compound has from about 5% to about 50% w/w of the ampholyte pendant groups per total compound.

5. A polymer comprising a polymerization product of an ampholyte monomer represented by a general formula (i):

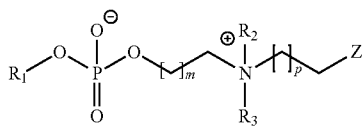

wherein $R_1$ is hydrophilic and chosen from the group consisting of (a) a substituted alkyl group, (b) a substituted cycloalkyl group, (c) a substituted cycloalkenyl group, (d) a substituted or unsubstituted heterocycle group, and (e) a substituted alkenyl group, wherein the $R_1$ group terminates with a methoxy group;

wherein $R_2$ and $R_3$, are independently chosen from the group consisting of
(a) a substituted or unsubstituted alkyl group, (b) a substituted or unsubstituted aryl group, (c) a substituted or unsubstituted cycloalkyl group, (d) a substituted or unsubstituted cycloalkenyl group, (e) a substituted or unsubstituted heterocycle group, and (f) a substituted or unsubstituted alkenyl group;

wherein m and p independently range from 0 to 6, with an m of 1 to 6 denoting a hydrocarbon chain referred to as the m-hydrocarbon chain and a p in a range from 1 to 6 denoting a hydrocarbon chain referred to as the p-hydrocarbon chain;

wherein the m-hydrocarbon chain and/or the p-hydrocarbon chain are substituted or unsubstituted hydrocarbon chains, wherein if the hydrocarbon chain is substituted substitution is an attachment to the hydrocarbon chain or is a heteroatom within the hydrocarbon chain; and wherein Z represents a polymerizable group comprising a vinylic or allylic group that is capable of undergoing free radical polymerization.

6. The polymer of claim 5 wherein Z is chosen from the group consisting of acrylates and methacrylates.

7. The polymer of claim 5 comprising a polymerization product of the ampholyte monomer of general formula (i) and a monomer of general formula (ii):

wherein X' represents a hydrogen or a methyl, Y' represents an oxygen in an ester moiety or a secondary amine in an amide moiety, and R' represents a member of the group chosen from (a) a substituted or unsubstituted alkyl group, (b) a substituted or unsubstituted aryl group,(c) a c substituted or unsubstituted cycloalkyl group, (d) a substituted or unsubstituted cycloalkenyl group, (e) a substituted or unsubstituted heterocycle group, and (f) a substituted or unsubstituted alkenyl group.

8. The polymer of claim 7 further comprising a polymerization product of the ampholyte monomer of general formula (i) and the monomer of general formula (ii) and a monomer of general formula (iii):

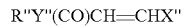

wherein X" represents a hydrogen or a methyl, Y" represents an oxygen in an ester moiety or a secondary amine in an amide moiety, and R" represents a member of the group chosen from (a) a substituted or unsubstituted alkyl group, (b) a substituted or unsubstituted aryl group,(c) a substituted or unsubstituted cycloalkyl group, (d) a substituted or unsubstituted cycloalkenyl group, (e) a substituted or unsubstituted heterocycle group, and (f) a substituted or unsubstituted alkenyl group.

9. The polymer of claim 5 comprising a polymerization product of the ampholyte monomer of general formula (i) and a monomer of general formula (iv):

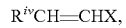

wherein X represents a hydrogen or a methyl, and wherein $R^{iv}$ is chosen from the group consisting of (a) an alkyl group, (b) an aryl group, (c) a cycloalkyl group, (d) a cycloalkenyl group, (e) a heterocycle group, (f) an alkenyl group, and (g) an alkyl tertiary amine group.

10. The polymer of claim 5 wherein the polymer has from about 5% to about 50% w/w of the ampholyte monomer per total polymer.

11. The polymer of claim 5 wherein m=1 and p=1 or 2.

12. The polymer of claim 5 further comprising a polymerization product of the ampholyte monomer of general formula (i) and at least one monomer chosen from the group consisting of acrylates, methacrylates, 2-hydroxyethyl methacrylate, hydroxypropyl methacrylate, n-butyl methacrylate, tent-butyl methacrylate, n-hexyl methacrylate, 2-methoxyethyl methacrylate, poly(hexanide) methacrylate, poly(hexanide) polyethylene oxide methacrylate, or alkyl derivatized poly(hexanide) methacrylate, acrylic, methacrylic acid, epoxy/glycidyl, heparin derivatized polyethylene oxide macromer, vinyl sulfonic acid monomer, monomers comprising poly(ethylene glycol), N-vinyl pyrrolidone monomers, 4-benzoylphenyl methacrylate, allyl methyl carbonate, allyl alcohol, allyl isocyanate, and methacryloyloxyethyl phosphorylcholine.

13. The polymer of claim 5 further comprising a polymerization product of the ampholyte monomer of general formula (i) and at least one methacrylate monomer.

\* \* \* \* \*

UNITED STATES PATENT AND TRADEMARK OFFICE
CERTIFICATE OF CORRECTION

PATENT NO. : 10,251,982 B2
APPLICATION NO. : 15/429835
DATED : April 9, 2019
INVENTOR(S) : Fanny Burrows et al.

It is certified that error appears in the above-identified patent and that said Letters Patent is hereby corrected as shown below:

In the Claims

Column 32, Line 22, please delete "R'Y'(CO)CH=CHX'" and insert -- R'Y'(CO)CX'=$CH_2$ --

Column 32, Line 39, please delete "R"Y"(CO)CH=CHX" and insert -- R"Y"(CO)CX" = $CH_2$ --

Column 32, Line 54, please delete "$R^{iv}$CH=CHX" and insert -- $R^{iv}$CX=$CH_2$ --

Signed and Sealed this
Tenth Day of September, 2019

Andrei Iancu
*Director of the United States Patent and Trademark Office*